United States Patent
Amini

(10) Patent No.: US 6,553,838 B2
(45) Date of Patent: Apr. 29, 2003

(54) DETECTION OF ANOMALIES ON RAILROAD TRACKS

(75) Inventor: Bijan K. Amini, Houston, TX (US)

(73) Assignee: Em-Tech LLC, Houston, TX (US)

( * ) Notice: Subject to any disclaimer, the term of this patent is extended or adjusted under 35 U.S.C. 154(b) by 16 days.

(21) Appl. No.: 09/940,364

(22) Filed: Aug. 27, 2001

(65) Prior Publication Data

US 2002/0033049 A1 Mar. 21, 2002

Related U.S. Application Data

(60) Provisional application No. 60/228,325, filed on Aug. 25, 2000.

(51) Int. Cl.$^7$ .............................................. G01N 29/04
(52) U.S. Cl. ............................... 73/636; 73/643; 73/644; 73/578
(58) Field of Search ......................... 73/636, 643, 644, 73/578, 862.333

(56) References Cited

U.S. PATENT DOCUMENTS

| | | | |
|---|---|---|---|
| 3,574,458 A | 4/1971 | Hollis | 355/80 |
| 3,617,779 A | 11/1971 | Rosenberg | 327/514 |
| 3,851,236 A | 11/1974 | Dennhardt | 388/316 |
| 3,962,908 A * | 6/1976 | Joy | 73/636 |
| 3,995,835 A | 12/1976 | Clichy | 366/273 |
| 4,174,636 A * | 11/1979 | Pagano | 73/636 |
| 4,468,966 A * | 9/1984 | Bradshaw | 73/636 |
| 4,679,936 A | 7/1987 | Gerharz | 356/128 |
| 5,038,107 A | 8/1991 | Gianzero | 324/339 |
| 5,132,623 A | 7/1992 | De | 324/338 |
| 5,150,446 A | 9/1992 | Penner | 385/122 |
| 5,260,661 A | 11/1993 | Vail | 324/339 |
| 5,283,520 A | 2/1994 | Martin | 324/220 |
| 5,426,367 A | 6/1995 | Martin | 324/221 |
| 5,610,517 A | 3/1997 | Ma | 324/233 |
| 5,619,423 A * | 4/1997 | Scrantz | 702/51 |
| 5,633,182 A | 5/1997 | Miyawaki | 438/30 |
| 5,654,639 A | 8/1997 | Locatelli | 324/339 |
| 5,698,977 A | 12/1997 | Simpson | 324/209 |
| 5,751,144 A | 5/1998 | Weischedel | 324/240 |
| 5,942,894 A | 8/1999 | Wincheski | 324/220 |
| 5,969,254 A | 10/1999 | Yamaguchi | 73/602 |
| 6,008,657 A | 12/1999 | Suyama | 324/639 |
| 6,025,721 A | 2/2000 | Vail | 324/368 |
| 6,064,428 A * | 5/2000 | Trosino et al. | 348/128 |
| 6,084,403 A | 7/2000 | Sinclair | 324/221 |
| 6,097,532 A | 8/2000 | Harris | 359/326 |
| 6,100,696 A | 8/2000 | Sinclair | 324/338 |
| 6,157,195 A | 12/2000 | Vail | 324/368 |
| 6,262,573 B1 | 7/2001 | Wojnarowski | 324/217 |
| 6,347,550 B1 * | 2/2002 | Kroening et al. | 73/598 |
| 2001/0019263 A1 | 9/2001 | Kwan | 74/548 |

* cited by examiner

Primary Examiner—Daniel S. Larkin
Assistant Examiner—Jacques Saint-Surin
(74) Attorney, Agent, or Firm—David McEwing

(57) ABSTRACT

The present invention relates to a method and apparatus for detecting anomalies, defects or electromagnetic properties of electrically conductive and magnetically permeable materials by using a magnet to partially saturate the material, thereby lowering its permeability, and sending a second, higher frequency oscillating electromagnetic wave into the material. The oscillating magnetic flux field permeating into the electrically conductive material induces eddy waves. As the apparatus passes over the material, the properties of the induced eddy currents, and the corresponding magnetic flux field induced by such eddy currents, changes as the properties of the material change. These changes can be the result of defects or anomalies in the material or in connecting welds.

27 Claims, 18 Drawing Sheets

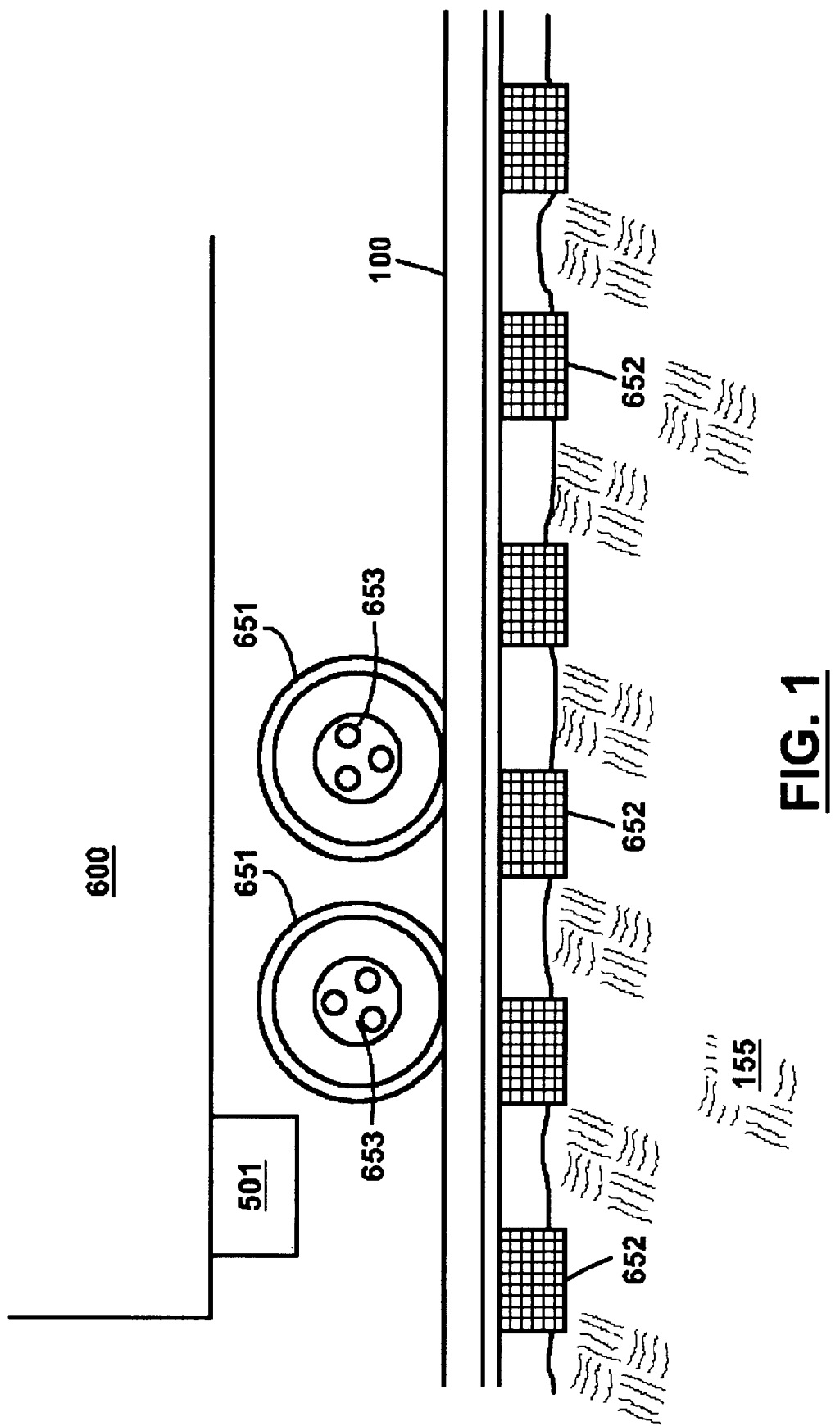

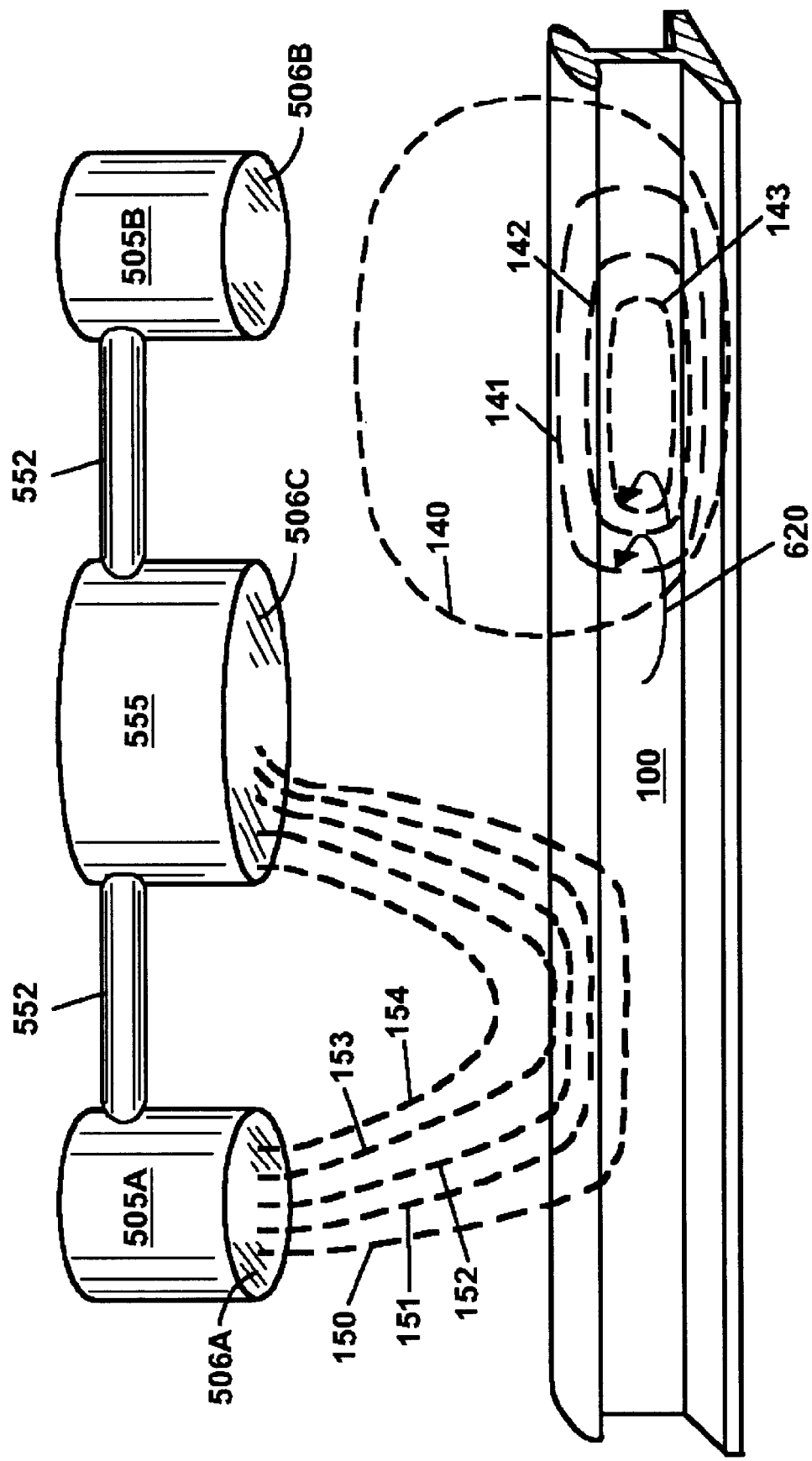

DETECTION OF ANOMALIES ON RAILROAD TRACKS

CROSS REFERENCE TO RELATED APPLICTION

This application claims the benefit of U.S. Provisional Application No. 60/228,325 entitled "Detection of Anomalies on Railroad Tracks at High Speed" and filed Aug. 25, 2000.

BACKGROUND OF INVENTION

1. Field of Use

Train derailments are a common and everyday occurrence, causing significant injury to persons and property. A common cause of derailments is a heavy moving train passing over a section of weakened or otherwise defective railroad track. The railroad tracks are commonly made of some form of carbon steel or other ferromagnetic material. Sections of rail are placed end to end and welded together to form a single, continuous rail. Each rail is also bolted or nailed on cross tie supports, i.e., railroad ties, providing support for the rails and maintaining the proper space between the separate but parallel rail tracks.

After time and use, various components of the railroad track begin to fail. The weakening of the rail track may continue and eventually result in a failure causing a railroad derailment. The weakening of the railroad track is evidenced by cracks forming within the steel rail or in the welded joints between separate rail sections. It is also evidenced by other deformations in the steel tracks. However, it is difficult to detect cracked or weakened rail sections prior to the occurrence of a derailment.

2. Description of Related Art

Current methods for the detection of cracks, defective welds or other anomalies in railroad tracks use Electromagnetically generated acoustic pulses. These pulses travel to a crack and their reflection is detected by sensors placed close to the rail surface. See U.S. Pat. No. 5,760,307. Such methods are, however, slow and require the sensors to be in very close proximity to the rail surface, typically within fractions of an inch.

BRIEF DESCRIPTION OF THE INVENTION

The invention subject of this application creates a completely new type of rail inspection device that can be installed on every locomotive. The subject invention can be used on a locomotive traveling at full speed of 80 plus miles per hour at a location 10 inches to 18 inches or more above the track surface. This device is completely enclosed in metal or other material to protect its sensors from high-speed debris impacts and elements of weather. The present invention can also be used in conjunction with Global Positioning Satellite (GPS) systems to catalogue the signature and location of each detected anomaly. Further, the energy requirements of the present invention can be on the order of tens of watts.

BRIEF DESCRIPTION OF THE DRAWINGS

The accompanying drawings which are incorporated in and constitute a part of the specification, illustrate preferred embodiments of the invention and, together with the general description of the invention given above and the detailed description of the preferred embodiments given below, serve to explain the principles of the invention.

FIG. 1 illustrates the possible location and relative size of the crack detection sensor of the present invention.

FIG. 9B illustrates the magnetic flux induced by eddy currents within the target rail.

Figure 2A:
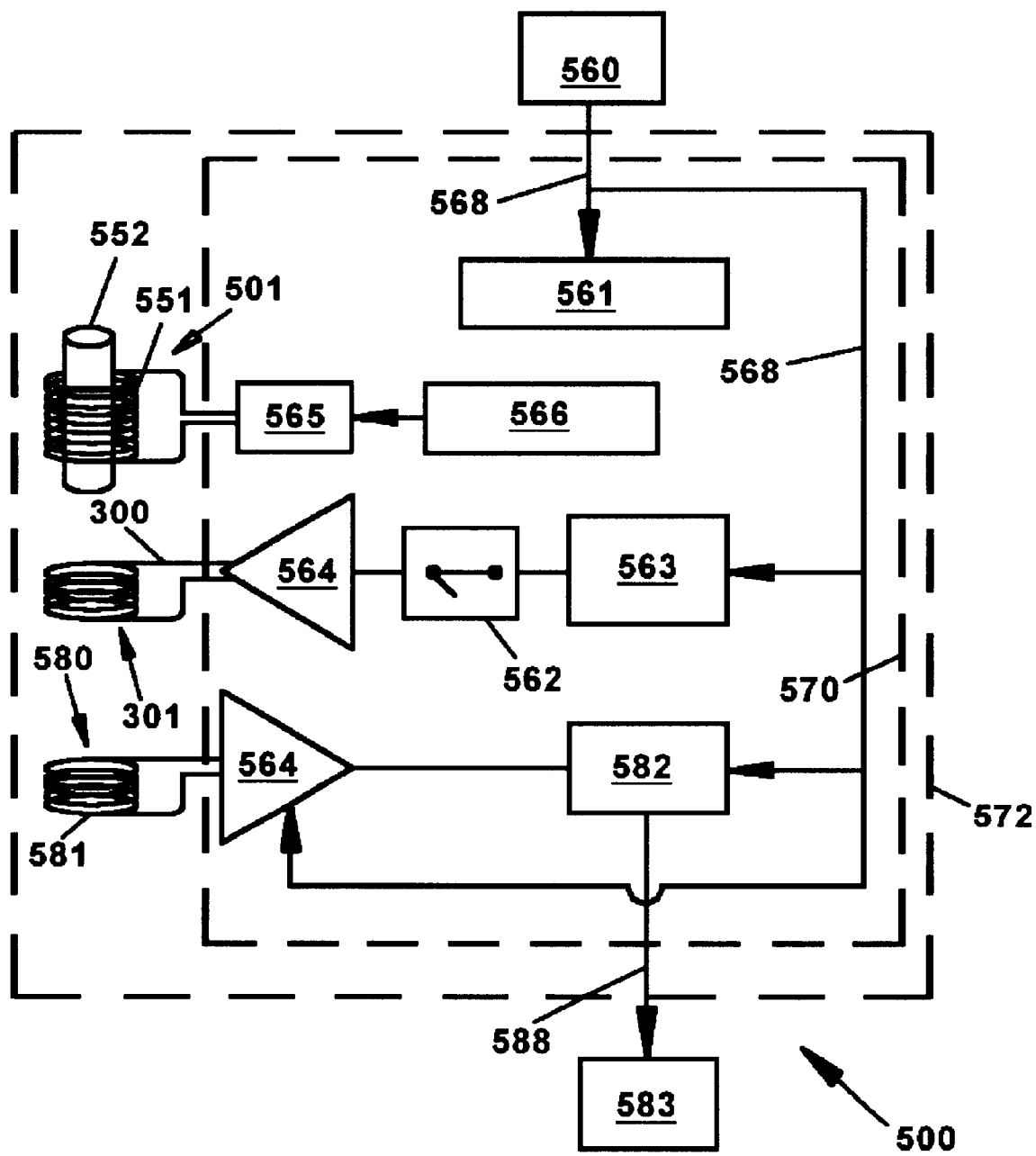
FIGS. 2A and 2B are schematic illustrations of the electronic components of the invention.

The above general descriptions and the following detailed descriptions are merely illustrative of the generic invention and additional modes, advantages, and particulars of this invention will be readily suggested to those skilled in the art without departing from the spirit and scope of the invention.

DETAILED DESCRIPTION OF THE INVENTION

The present invention may be mounted on a rail car or locomotive approximately 10 to 18 inches (or more) above the steel railroad track. The present invention includes the creation of transparencies or windows ("Metallic Transparency"™ regions) within the steel railroad track, thereby allowing oscillating magnetic flux to penetrate into the steel railroad track.

In one embodiment, the present invention is described by the following steps: (1) a saturation component (magnetic saturation generator) containing a "saturation coil", preferably wrapped around a highly permeable core ("saturation core"). When the saturation coil is energized, it acts as an electromagnet. The saturation coil creates one or more fields of magnetic flux ("saturation flux") adjacent or near the railroad track. The saturation flux engages with the adjacent railroad track and creates a partial magnetic saturation of the railroad track proximate to the saturation coil. Saturation results in the magnetic permeability of the railroad track being substantially lowered. When partially saturated, the railroad track acquires greater capacity to engage or couple with magnetic flux, especially magnetic flux oscillating at relatively high frequencies. (When fully saturated, that portion of the railroad track cannot absorb further magnetic flux, thereby allowing additional flux to pass through the railroad track.) When in a state of partial magnetic saturation, that portion of the railroad track (and particularly the surface portion of the railroad track) has become "transparent" to magnetic flux. This partially saturated section is known as a "transparency" or a "Metallic Transparency" region. (2) One or more magnetic flux transmitter components ("transmitters"), each utilizing one or more coils ("transmitter coil") located proximate to a metallic transparency region, then create one or more fields of additional magnetic flux oscillating at frequencies preferably equal to or greater than the saturation flux. This oscillating magnetic flux ("transmitter flux") is engaged with the section of partially saturated railroad track (having significantly reduced magnetic permeability) allowing the oscillating transmitter flux to penetrate into, i.e., engage with, the track. It will be appreciated by persons skilled in the art that if the permeability of the steel railroad track is not significantly reduced, most (if not all) of the oscillating magnetic flux will transmitted across the air gap will not adequately penetrate into or engage with the track. The oscillating magnetic flux will induce electrical eddy currents within the rail. These electrical currents are conducted through the electrically conductive track. (3) Through basic electromotive forces, the oscillating eddy current will induce a separate oscillating magnetic flux within the track. (4) The field of this induced magnetic flux can extend out from the track. As in step No. 1 above, the same or similar saturation coils create a region of reduced permeability within the track near a separate coil ("receiver coil") so that the induced magnetic flux within the track can be detected and measured by this receiver coil. (5) The receiver component, of which the receiver coil is part, converts the induced flux ("receiver flux") into electrical signal ("receiver current") that are filtered and processed in order to determine the electrical resistivity and other properties of the steel railroad track. The receiver flux is electrically processed to concentrate and magnify the induced oscillating magnetic flux, thereby forming the receiver current. The transmitter flux is nulled to minimize direct transmission of flux from the transmitter to the receiver. The transmitter flux is compared to the received flux and, using the changes in amplitude and phase, the electrical resistivity or other properties of the track is determined and displayed. These signals may then be sent to the output display for further processing, display, and recording.

Accordingly, the method and apparatus of the invention includes the capability of generating magnetic flux ("saturation flux") to engage and partially magnetically saturate a portion of the railroad track, thereby creating a Magnetic Transparency region. The invention also includes the capability to generate and transmit one or more separate oscillating magnetic flux ("transmitter flux") into the Metallic Transparency region created in the railroad track. The invention also includes the capability to receive and measure any magnetic flux ("receiver flux") induced in the railroad track.

As will be discussed in greater detail below, the preferred embodiment of the invention will include the ability to generate and send a plurality of transmitter flux of differing frequencies, either simultaneously or sequentially. A preferred embodiment will also include the ability to detect and measure receiver flux from a plurality of directions. A preferred embodiment will also have the capability to partially saturate one or more portions of a separate component comprising an electrically conductive and magnetically permeable material, i.e., a barrier material or EM barrier, in order that one or more frequencies of oscillating magnetic flux may be induced and focused or directed into the railroad track creating a Magnetic Lensing™ focus.

A preferred embodiment of the invention will also incorporate one or more means to null direct coupling of magnetic flux between the transmitter and receiver, i.e., the direct transmission of the transmitter flux to the receiver coil. In addition, a preferred embodiment of the invention will include means to accurately measure the track properties, e.g., conductivity, permeability and thickness. These changes can be used to detect defects, cracks or other anomalies within the track.

It will be appreciated that there is a plurality of components or subsystems in the invention. By way of example, such sub-systems include the following: Magnetic Saturation Generator, Transmitter/Receiver System, Nulling System—geometric, electronic, permeability, Automatic Lensing System, Conductivity/Resistivity Measurement System and Rail Thickness Measurement System. All or some of these subsystems may be incorporated into a preferred embodiment of the tool subject of this invention. Examples of selected embodiments will be discussed in greater detail below.

1. Magnetic Saturation Generator

The design of the saturating magnetic flux system (hereinafter "magnetic saturation generator") allows the reduction of the permeability of the adjacent portion of track. It will be appreciated by those skilled in the technology that the barrier material comprising the railroad track, e.g., carbon steel, may have relative permeability in excess of 10,000 at a typical magnetic flux density. A near fully saturated portion of the track is, however, transparent to the transmission of additional magnetic flux. (When in a state of full saturation, the fully saturated or transparent portion of the track can not absorb further magnetic flux. Therefore, a second and oscillating magnetic flux from the transmitter of the invention will penetrate through the fully saturated track and into the ground or structure beneath the track.) The depth of penetration of the oscillating magnetic flux across the air gap and into the rail is proportional to the separation distance between the transmitter and receiver of the invention. A series of receivers placed at varying distances from a single transmitter could establish various depths of measurement directionally into the railroad track structure proportional to these separations. It will be noted, however, that as the separation distance "D" between the transmitter and receiver(s) is increased, the density of the flux decreases at a rate of $1/D^3$. It is important that the cross sectional area of the magnetic saturation generator core, e.g., saturation core or culminator, not become completely saturated. When fully saturated, i.e., permeability ($\mu$)=1, magnetic flux may be randomly emitted from the saturated material surface into the adjoining media, i.e., air, in forming the closed magnetic flux loop between the opposing magnetic poles.

In one embodiment of the invention, a separate component also comprising an EM barrier, is partially saturated for creating a Magnetic Antenna™ component. When in a state of partial saturation, the antenna component can be used for creating a Magnetic Lens™ focus, thereby directing oscillating flux into the railroad track. Simply stated, when an EM barrier is partially saturated, the permeability of the barrier material is substantially reduced, thereby allowing greater penetration by the oscillating transmitter flux, particularly at higher frequencies. However, the relative permeability of the barrier material (the antenna) is greater than 1. The partially saturated antenna continues to absorb a significant portion of the transmitter flux. Since the antenna is also electrically conductive, eddy currents are generated within the antenna. These eddy currents induce a separate oscillating magnetic flux. At least some portion of the magnetic flux from this induced magnetic field is transmitted out from the partial barrier material comprising the antenna. However, the lines of flux are bent or altered as they are emitted out from the surface of the partially saturated material into the surrounding environment. This bending of magnetic flux is can be controlled, allowing the lines of magnetic flux to be focused on the railroad track proximate to the opposite side of the antenna from the magnetic saturation generator. This focusing partially counteracts the normal rapid geometric spreading of magnetic flux. It will be appreciated that the component of the magnetic saturation generator itself maybe used to create the magnetic lens focus with a separate antenna component.

Concentrating the magnetic flux allows distant sensing using much less power. This allows measurement of electrical resistivity and other properties of the railroad track more efficiently than can be achieved by controlling the separation distance between the transmitter and receiver. When utilized in this manner, the magnetic saturation generator includes the Magnetic LenS™ focus capability.

2. Transmitter/Receiver System

There are many transmitter/receiver configurations and orientations.

(a) Transmitter—There may be more than one transmitter arranged directionally proximate to the railroad track. In addition, multiple separate transmitter flux of the same frequency may be used to generate separate eddy currents bucked with respect to each other to propagate the eddy current further out into the track ahead of the train. This bucking or interaction among magnetic flux oscillating at the same frequency may be used to direct transmitter flux in a controlled manner. A plurality of transmitters may also be configured to achieve a desired transmitter flux geometry.

(b) Receiver—There may be a plurality of receivers used in an evenly or unevenly spaced array. The windings of separate receiver coils may be bucked or used to enhance the flux or establish directionality of received fluxes.

3. Nulling System

The receiver system may be nulled with respect to the transmitter system. This nulling prevents the receiver system from being overwhelmed by the flux emitted from the transmitter system. It also minimizes the interference of any extraneous electrical flux, i.e., electrical noise. It has been found that a combination of three nulling techniques provides the best results. These three systems are (a) geometric, (b) electronic, and (c) transmitter flux absorption by permeability.

(a) Geometric nulling—A wide combination of geometric nulling systems may be used. The respective design and location of each transmitter and receiver may vary in consideration of the placement and design of the other transmitters or receivers and in consideration of the location and geometry of the track or partial transparency region. Therefore, by not wrapping either the transmitter or receiver coils, or both, around the magnetic saturation generator allows a number of advantages. These are:

1. Mechanical nulling by receiver or transmitter placement or rotation with respect to each other, or with respect to the track.
2. Directionality by being nearest the track side of the saturation core, or by rotation of the axis of the transmitter or the receiver.
3. Minimizing possible saturation of the magnetic saturation generator core that would cause uncontrolled dispersion of saturation flux. The dispersed saturation flux may achieve only partial saturation of a selected portion of the railroad track. This may be a desired result. This is exactly opposite the concern cited in U.S. Pat. No. 5,038,107 which does not want to use an ac current on the magnetic saturation generator core that may take the target or core out of saturation.
4. Since the transmitter coil can have an air core, laminated core or smaller inductor core than the magnetic saturation generator core, much higher frequencies can be used for the transmitter flux. This is due to the inductive impedance resulting from the presence of a large metallic saturation core. This large saturation core drives up the total impedance.
5. Multiple transmitters, each at different frequencies, may broadcast simultaneously to perform spectroscopy over a large frequency range.
6. Transmitters comprised of differing coil geometry will have differing flux geometry. Therefore varying the design of the transmitter, e g., varying the coil length, may also be used to control the portion of the track that will be investigated.
7. The transmitters and receivers must be placed in sufficient proximity to the partially transparent region to facilitate the transmission of either transmitter flux or receiver flux into or from the track across the air gap between the track surface and the tool of the this invention.
8. Multiple transmitters can be used to "buck" each other, thereby causing the geometry of the transmitter flux to be altered. Transmitters may also be configured in order that separate but opposite eddy currents are generated within the track, thereby causing the currents to buck each other. This may achieve a greater penetration or transmission of the eddy currents into the surrounding track ahead of the train.
9. Multiple receivers can be either nulled with respect to each other and/or built into an array for improving flux-receiving resolution. These techniques may incorporate reversing the direction of at least one of the transmitter coils or altering the length of at least one of the transmitter coils in relation to the other(s).

(b) Electronic nulling—In this nulling type, it is possible to either null by creating a receiver flux 180° out of phase and exactly in reverse amplitude to the transmitter flux. Another method is measuring the receiver flux attributable to direct coupling of the transmitter flux and subtracting this value from all other measured values of receiver fluxes.

Another variation of electronic nulling may involve distinguishing the signal attributable to the electrical properties of the rail proximate to the sensor tool from the received signals attributable to distant sections of rail. This may be accomplished by measuring the signals received from a transmitter and receiver combination used without a saturation coil. In this configuration, the oscillating transmitter flux, preferably at a relatively low oscillation frequency, will generate eddy currents within the rail. The magnetic flux induced by eddy currents can be detected and measured by the receiver. The values recorded by this receiver can be compared and, in one methodology, be subtracted from the values recorded by the receiver utilized in conjunction with the magnetic saturation flux generator. This receiver (used in conjunction with the saturation flux generator) will be receiving signals induced by the eddy currents generated by the oscillating transmitter flux penetrating into the rail proximate to an area partially saturated by the dc or low frequency magnetic saturation flux. This transmitter flux will generate detectable eddy currents throughout a much larger portion of the rail that the transmitter flux used without benefit of partially saturation of the rail. Therefore, this nulling provides a basis to distinguish between signals indicative of rail conditions proximate to the sensor tool and signals indicative of significantly more distant rail conditions (c) Permeability nulling—In this nulling method, a variety of ways may be used to absorb the transmitter flux before it reaches the receiver. This may be accomplished by separating the transmitter and receiver by enough high permeability material to absorb the transmitter flux before it reaches the receiver coil. Another absorption method is to isolate the transmitter from the receiver by highly permeable materials such as EM barriers or by placing the receiver coil a large enough distance from the transmitter such that the transmitter flux is absorbed prior to reaching the receiver coil.

4. Automatic Lensing System

One variation of the invention utilizes an oscillating transmitting current penetrating through and emanating out of the partially saturated core of the magnetic saturation generator upon which the transmitter coil may be wound. This core may comprise the culminator proximate to the target rail. The oscillating transmitter flux induces eddy currents within the electrically conductive and magnetically permeable material i.e., barrier material or EM barrier, comprising the culminator located above the target rail. As already discussed, when partially saturated, the magnetic permeability of the barrier material is lowered. As the permeability is lowered, it begins to approach the magnetic permeability of air. For air, $\mu_{(air)}=1$. As the permeability of that portion of the culminator surface approaches 1, the angle of flux lines emanating from the culminator surface begins to shift or decrease from 90° to the culminator surface. As it is generally known that separate magnetic flux lines repel and can not cross, the shift pushes the adjoining flux lines over, resulting in the redirection of the flux. This directionality can be controlled by the degree of saturation of the culminator. Of course, the level of saturation is a combination of the transmitter flux and saturation flux and changing either component will alter the saturation level of the culminator. Directionality may also be controlled in combination with the geometry of the saturation core, including the culminator surface, the placement of the transmitter coils and saturation coils, and the dc or ac current levels.

Magnetic lens focus may also be achieved by the partial saturation of a separate barrier material. This EM barrier may be the bottom portion of the tool housing and partially saturated by the magnetic flux generator. When partially saturated, oscillating transmitter flux will generate eddy currents within the material. The barrier material, now containing eddy currents, which induce a separate oscillating magnetic flux, serves as a magnetic antenna. The eddy currents induced within this antenna induce a separate oscillating magnetic flux that is emitted out from the antenna and couples with the rail. The composition or geometry of the antenna, as well as the transmitter frequency, may be used to direct or control the oscillating magnetic flux, thereby facilitating this coupling and retarding the otherwise rapid dispersion of the magnetic flux.

It will be readily appreciated that this oscillating magnetic flux, coupled or engaged with -the rail, will generate a separate eddy current within the rail, which, in turn, will induce an oscillating magnetic flux that can be detected by a receiver coil. The reception of the flux may also utilize the antenna created in the preceding paragraph. It will further be appreciated that the properties of this induced flux will vary as a result of the physical conditions of the rail in which the eddy current is generated and that these variations may be measurable.

In applications wherein the rail is partially saturated by the flux of magnetic saturation generator, in conjunction with the enhanced coupling with the oscillating transmitter flux, the resulting field of induced oscillating magnetic flux radiates out of the partially saturated track and may be detected by the receiver coil of the tool. (Of course as appreciated by persons skilled in the art, this oscillating magnetic flux will generate separate eddy currents within the electrically conductive receiver coil and this electric current will be used to measure the properties of the rail.)

In this manner, the rail may also serve as an antenna for the transmission of oscillating magnetic flux. This can achieve a signal, detectable by the receiver of the tool, that can reveal defects or cracks in the rail far in advance of the tool subject of this invention. It will be appreciated that since full saturation is not required, the energy requirements are decreased.

There is a relationship between the amount of power utilized by the magnetic saturation generator required to achieve partial saturation and the power utilized by the transmitter. This relationship can be used to optimize the Magnetic Lensing focus effect and the strength of the receiver flux. When the transmitter and receiver are separated in a bistatic configuration, it has been found that optimized flux strength is achieved by increasing the saturation flux proximate to the receiver by as much as a factor of four over the power utilized to create the partial transparency proximate to the transmitter. This enhances the transparency of the track proximate to the receiver. This relationship between the magnetic flux for the receiver and transmitter can be derived by known methods. This relationship will vary as the rail thickness permeability; rail conductivity or other characteristics vary.

5. Conductivity, Permeability Measurement System

To perform accurate measurements of the properties of the railroad track, the track electrical conductivity and magnetic permeability must be understood.

(a) The conductivity is measured in the track by analyzing the frequency spectral response over a sufficient range to measure the effects of conductivity on the various frequencies.

(b) The permeability of the track exhibits a relationship with the strength of the saturating coils. Therefore, at each measurement the power of saturation flux may be varied. The frequency of the flux, however, is maintained constant. The change in track permeability responsive to changes in the saturation flux density is monitored.

6. Rail Thickness Measurement System

Once the conductivity and permeability are determined, it is possible to determine the thickness of the rail. This ability is useful in the detection of worn or corroded sections of rail.

Reference will now be made in detail to the present preferred embodiments of the invention as described in the accompanying drawings.

FIG. 1 illustrates an embodiment of the tool 501 of the present invention in relation to a train car or locomotive 600 and a rail 100 is shown. The railroad ties 652, track bed 155, railroad wheels (or trucks) 651 and hubs 653 are also shown in relationship to the tool 501.

Figure 2B:
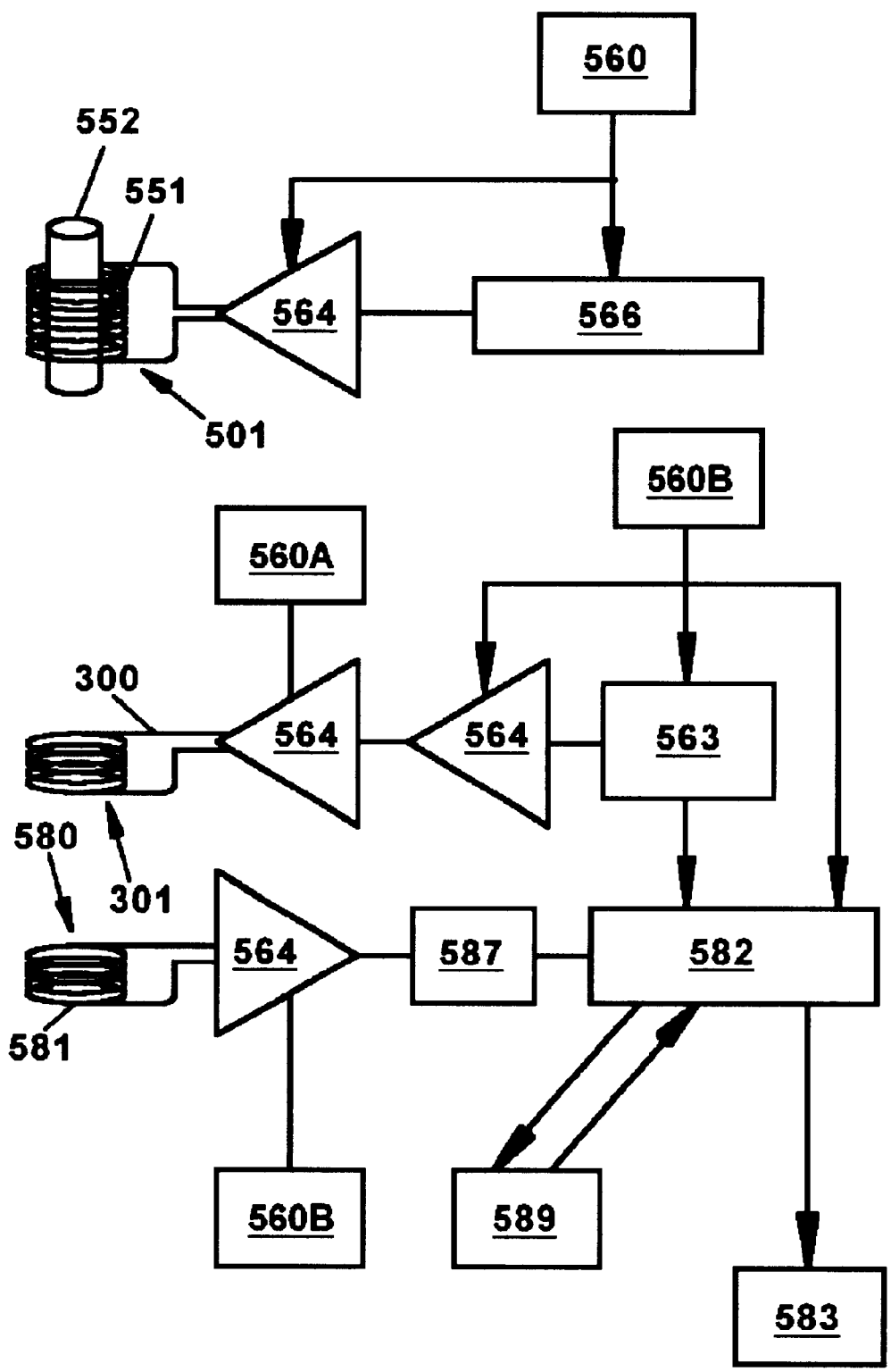

The interior working of one embodiment of the sensor tool 500 of the present invention is shown in FIGS. 2A and 2B. FIG. 2A illustrates schematically one embodiment of the components of the sensor tool 500 subject of the invention. The components of the tool 500 are contained within a tool housing 572. The tool 500 includes (a) a magnetic saturation generator 501 for creating a Metallic Transparency region within the railroad track and including one or more saturation coils 551, (b) a magnetic flux transmitter component 300, comprising the transmitter coil 301, a switch 562, and a low noise amplifier (LNA) 564, (c) a receiver component 580 for the detection and measurement of magnetic flux penetrating through the railroad track and comprising a receiver coil 581, (d) a frequency generator 563, (e) a pulser 566, (f) one or more capacitors 561 and (g) a nulling device 582. The magnetic saturation generator 501 includes the saturation coil 551, saturation core or magnetic culminator (not shown). The magnetic saturation generator 501, saturation coil 551, the transmitter 300, transmitter coil 301 and any associated core (not shown), the receiver 580, including the receiver coil 581; and the associated components described above and depicted within the sensor tool housing 572, can be maintained above the railroad track to minimize possible damage from debris thrown up from the railroad bed or railroad track as the train moves at a high rate of speed. The output display 583, operator controls (not shown) and power source 560 may be typically located within the train or locomotive compartment and linked to the tool housing 572 by means of standard cables and connectors 568 and 588. The operator's console or display 583 may also record and display historical trends of track properties and may be located remote from the train.

FIG. 2A illustrates an alternate embodiment utilizing a high voltage 560B and low voltage 560A power source. The low voltage power source may be utilized for the transmitter flux generator 300 and for the digital flux processor. The high voltage power source 560B may be used with an amplifier for desired amplification of the transmitter flux. A dc power supply 560 is preferably used for generating the saturation flux emitted from the saturation coil 551. It may also be found to be advantageous to utilize an analog to digital flux converter. It is envisioned that a digital flux converter, as well as other sub-components, may be contained within an electronic is component 570.

The saturation coil 551 is a principle element of the magnetic saturation generator 501. It may be utilized in conjunction with one or more transmitter components, receiver components, or combinations of both. The saturation coil 551 generates a magnetic flux that engages (or couples) with and saturates a portion of the railroad track. The transmitter coil 301 is a principle element of the transmitter component ("transmitter") 300. The transmitter 300 creates the oscillating magnetic flux ("transmitter flux") that engages with and is transmitted through a magnetically saturated portion of the railroad track (not shown).

When the railroad track is partially saturated with magnetic flux from the magnetic saturation generator, oscillating flux from one or more additional transmitters 300 may readily penetrate into (couple with) the railroad track. Preferably, the saturation coil 551 generates a low frequency or constant magnetic flux. The oscillating magnetic flux of the transmitter 300 will preferably be at a higher frequency, e.g., higher by a multiple of 10, than the frequency of the saturation flux. In a preferred embodiment of the invention, the transmitter has the capability to generate a plurality of separate magnetic flux, each having distinct frequencies.

The receiver 580 may be combined with a separate saturation coil 551, thereby allowing the receiver 580 to be placed away from the transmitter 300. This has a number of advantages, including facilitating nulling between the transmitter 300 and receiver 580. An embodiment of the tool 500 of the present invention in which the transmitter 300 and receiver 580 are located proximate to separate magnetic saturation generators is termed a "bistatic arrangement" or "bistatic configuration."

The saturation coil 551 and saturation core 552, the transmitter coil 301 and the receiver coil 581, are often depicted separately from the other components described above and depicted within the "electronics component" 570 in FIG. 2A. For clarity, many of the drawings contained within this specification do not depict the electronics component. Further, the drawings may show an illustration of a coil only, but may be variously labeled as a magnetic saturation generator, transmitter or receiver. It is understood that the other components or sub-components are deemed to be included as necessary. In addition, the components of the invention, including but not limited to the saturation coil 551, transmitter coil 301 and receiver coil 581 are not placed in physical contact with the railroad track.

Figure 3A:
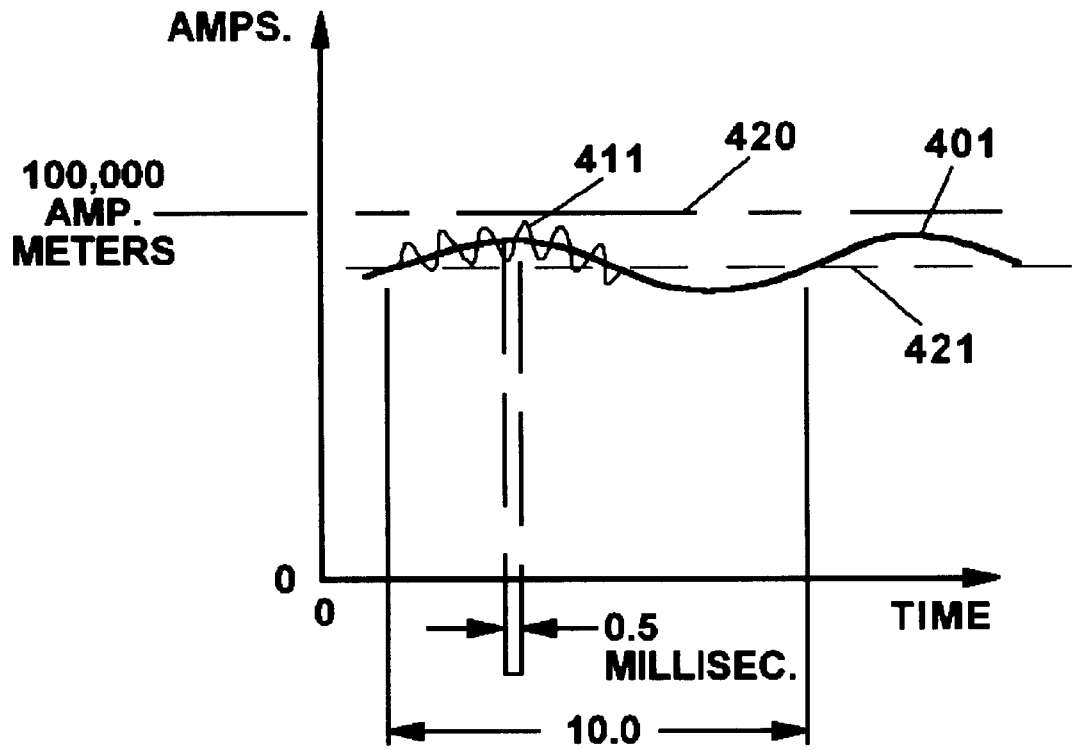
FIGS. 3A, 3B and 3C illustrate the relationship among the transmitter flux, saturation flux and the permeability of the target rail.

FIG. 3A illustrates a graph of current versus time with respect to the present invention. FIG. 3A illustrates three significant features in practicing the present invention: the level or quantity of saturation flux required to achieve the chosen level of saturation 420 within the track, the higher frequency transmitting flux 411 and, as compared with the transmitter flux, the lower frequency of the actual saturation flux 401. The higher frequency transmitter flux 411 is imposed on the lower frequency saturation flux 401. FIG. 3A illustrates the higher frequency oscillating transmitter flux as the spikes associated with the transmitting flux 411 disposed along a lower frequency oscillating saturation flux 401. In one embodiment of the present invention, the transmitter flux 411 may be transmitted only during the duration of each cycle of the oscillating saturation flux 401 that is above the selected level 421 of partial saturation. Among other advantages, the latter embodiment minimizes energy consumption. In the latter embodiment, it is possible to have multiple wavelengths ("oscillating flux transmissions") of transmitter flux 411 during each phase that the saturation flux 401 is within the selected saturation level (or range) 421.

The saturation flux 401 may not achieve the flux density necessary to achieve the selected level of saturation of the. targeted area of the EM barrier material comprising the rail. However, when partially saturated, a significantly greater portion of the distinctively higher frequency transmitter flux 411 will be able to couple, i.e., penetrate, into the railroad track to generate eddy currents. In another embodiment, the saturation flux 401 may be generated from at least one permanent magnet, a low frequency ac current or a direct current dc electromagnetic device.

Illustrated schematically as an apparatus in FIG. 2 and conceptually in FIG. 3A, the saturation coil 551 generates the saturation flux 401, which in turn creates the Metallic Transparency region in the track 100. The saturation coil is comprised of conductive material preferably wrapped around a highly permeable core (saturation core or flux circuit core) and powered either by dc current or a current oscillating at a low frequency. The transmitter flux 411 may be generated by the transmitter 300, comprised of the coil 301 of conductive material, powered by alternating current, preferably at a controlled frequency, wrapped upon or near the saturation coil 551. Preferably, the transmitter flux 411 is at a higher frequency than the saturation flux 401. It is preferred that the frequency of the transmitter flux 411 be at least a multiple of 10 greater than the frequency of the saturation (also termed saturation flux 401). As discussed above, the higher frequency of the transmitter flux 411 relative to the saturation flux 401 allows, for example, 10 wavelengths of the transmitter flux 411 to be emitted, and thereby couple with the rail, for inducing an oscillating magnetic flux within the rail. The detection and measurement of this separate oscillating flux may be dependant upon or occur only within the time period that the rail is within (or above) the required partial saturation level 421.

In FIG. 3A, the high frequency transmitter flux 411 is illustrated being pulsed at less than 0.5 millisecond rates. If the lower frequency saturation flux 401, generated by the saturation coil 551, is pulsed or activated "on" for 10 milliseconds 430, there is sufficient time for twenty transmitter pulses (e.g., with a wavelength period of only 0.5 millisecond) to couple with the partially saturated rail. As explained in the preceding paragraph, these 20 wavelengths of oscillating flux 411 emitted during the "on" pulse of the saturation flux 401 induce oscillating eddy currents that may be detected and measured by the receiver 580 located within the tool housing 572.

Figure 3B:
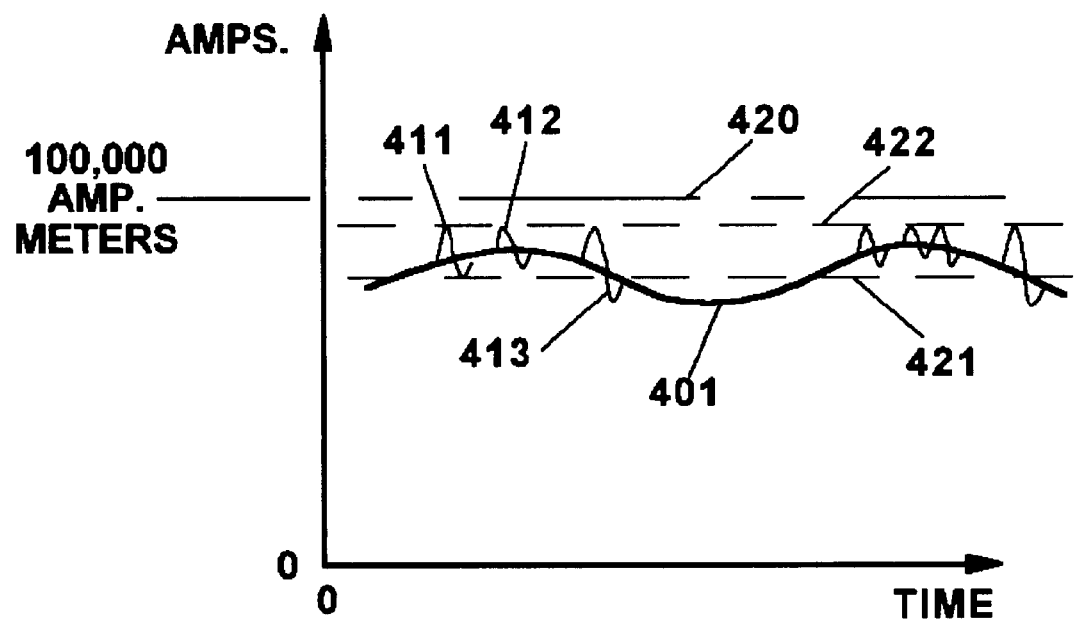
Figure 3C:
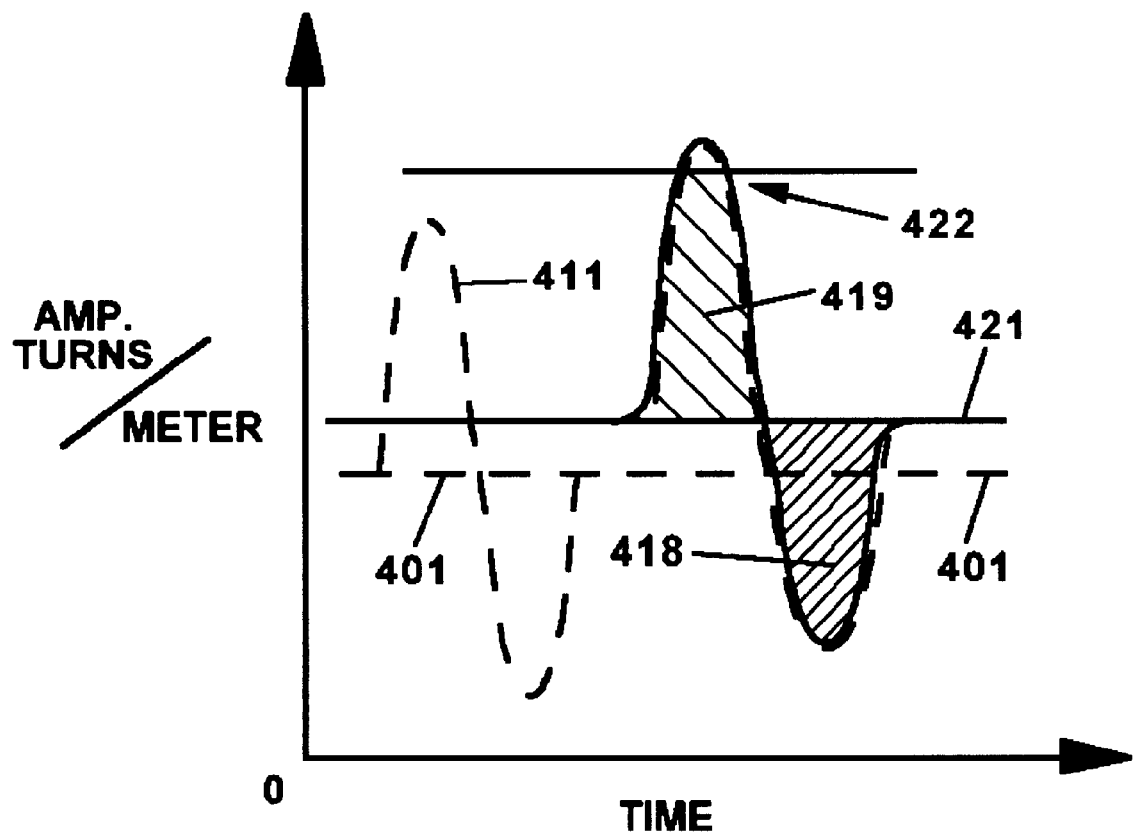

FIG. 3B illustrates varying the amplitude 412 and 413 of the transmitter flux 411 to compensate for the changes in the amplitude of the saturation flux 401, thereby allowing a sufficient level 422 of saturation or reduced permeability to be maintained. FIG. 3C illustrates the combine flux field 422 comprised of the higher frequency transmitter flux 411 and the saturation flux 401 may alternatively exceed the wide hatched curve 419 or fall below the small hatched curve 418 the level 421 of saturation selected to be created within the target rail.

For most applications utilizing the apparatus shown in FIG. 2, a power source 560 of 300 watts or less is sufficient to create the transmitter flux 411 and saturation flux 401. For thicker material, strong pulses and fluxes may be generated by utilizing the charge storing capacitors 561. The capacitors 561 are slowly charged then quickly discharged through a switch 562 and then through the low impedance large coil 551. At the same time, the higher frequency small flux coil 300 is pulsed.

With reference to the preceding discussion of the invention, one embodiment of the invention comprises the following steps and utilizes the referenced components and sub-components: (1) The saturation coil 551, when energized, acts as an electromagnet. The saturation coil 551 creates one or more fields of magnetic flux 401 adjacent or near the railroad track (not shown). The saturation coil 551 creates a partial magnetic saturation within a portion of the railroad track immediately proximate to the saturation coil 551. Saturation results in the magnetic permeability of the railroad track being substantially lowered. (2) The transmitter 300 then creates one or more fields of additional magnetic flux 411 having frequencies preferably equal to or greater than the saturation flux 401. The second field of magnetic flux 411 is engaged with the section of partial saturation (having greatly reduced magnetic permeability) allowing the transmitter flux 411 to pass into the transparency of the railroad track. (3) The electrically conductive properties of the rail interact with the oscillating magnetic flux 411 created by the transmitter 300. Through basic electromotive forces, an eddy current is generated within the electrically conductive rail and a separate oscillating magnetic flux is induced in the rail by this eddy current. (4) The induced magnetic flux extends out from the track rail. As in step No. 1 above, the same or similar saturation coils 551 create an area of reduced permeability, i.e., a transparency within the rail near the receiver 580 so that the magnetic flux induced within the rail can be detected and measured. (5) The receiver 580 converts the induced flux into electronic signals that are filtered and processed in order to determine the electrical properties of the rail. The received flux is processed using various electronic components (which may be located within the electronic component 570) to concentrate and magnify the reacted oscillating magnetic flux. The invention may contain means 582 to electronically null the transmitter flux to minimize direct transmission of flux from the transmitter 300 to the receiver 580 and to minimize the interference of electronic noise. The transmitted flux is compared to the received flux and, using the changes in amplitude and phase, the resistivity is determined and displayed. This signal is then sent to the output display 583 for further processing, display, and recording.

It is seen from FIGS. 4–7 that there are a number of ways to design the sensors. FIG. 4A illustrates a configuration having two saturation coils 551A and 551B wrapped around separate saturation cores 552A and 552B. The pole cores 504 and 505 of the combined electromagnets are comprised of large and highly magnetically permeable material. In this configuration, both pole cores 504 and 505 combine the like poles of the two separate electromagnets created by the saturation coils being wound on the saturation cores 552A and 552B. In this manner, these two cores 504 and 505, comprising or containing opposing poles, are each culminators. As discussed elsewhere, it is important that the cross sectional area of the poles (sometimes designated flanges) and saturation cores do not go into total saturation. The distance L between the pole cores 504 and 505 is twice the distance L/2 between the face of each pole core 506A and 506B and the surface of the target railroad track 100. It will be readily appreciated that as the distance L/2 increases, the amount of magnetic flux emitted from each pole 504 and 505 required to achieve the desired level of partial saturation of the rail 100 must increase, and that this increase in magnetic flux may require an increase in the size or permeability of the saturation cores 552A, 552B and the pole cores 504 and 505 in order that no part of the magnetic saturation generator 501 goes into saturation.

Figure 4A:
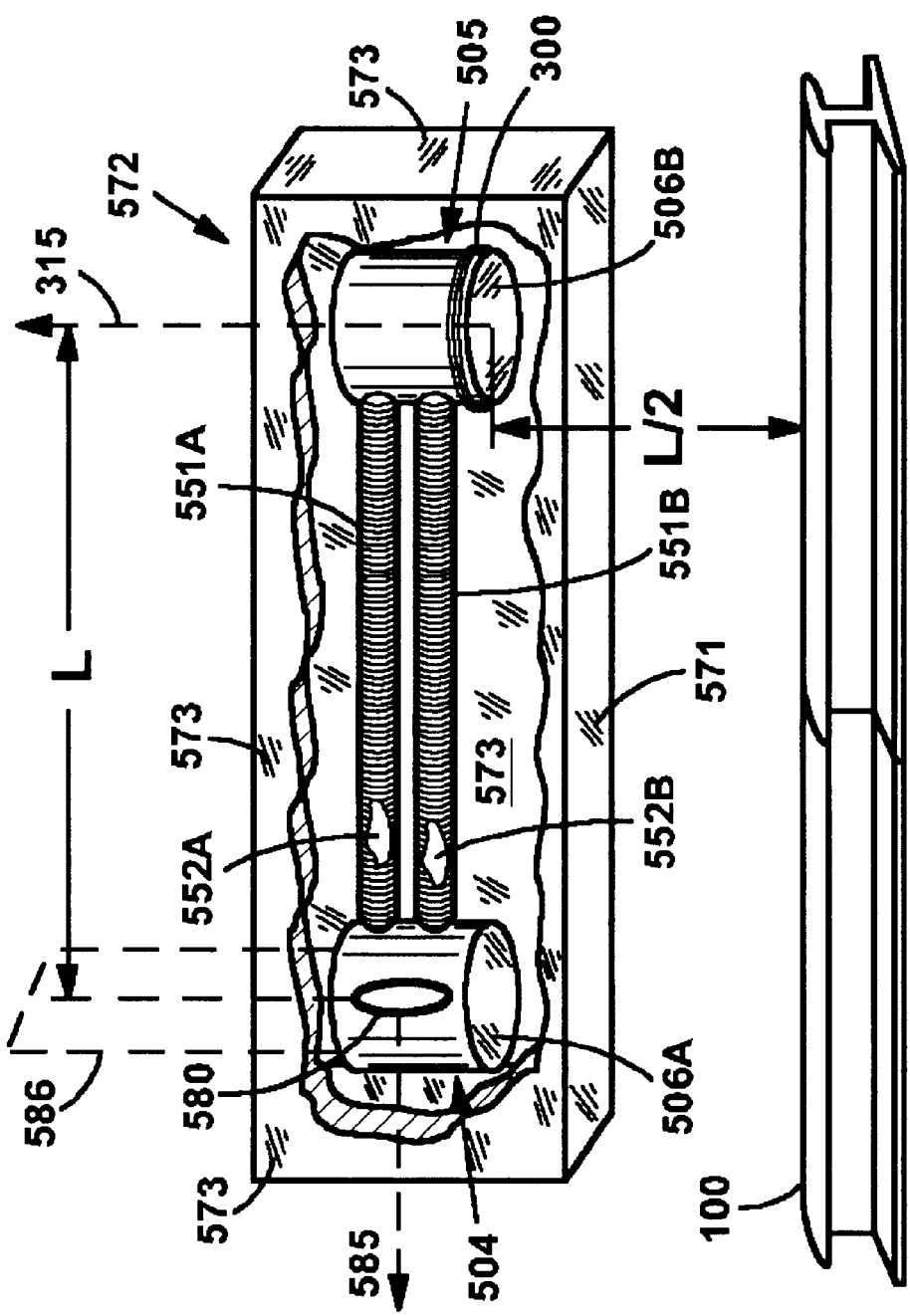
FIGS. 4A and 4B illustrate embodiments of the transmitter, receiver and magnetic coil arrangement.

In FIG. 4A, the transmitter coil 300 is wrapped around the exterior of core 505, thereby having the same magnetic moment region as the pole core. The receiver core 580 is wrapped around or within the opposing core 504 and having the geometric plane 586. The center axis 315 of the transmitter coil 300 is orthogonal to the center axis 585 of the receiver coil 580. The tool 501 is contained within a housing 572. Selected sides 573 of the housing may comprise EM barrier materials and provide EM shielding. The bottom of the housing 571 may be comprised of a plastic or similar material that is not magnetically permeable and electrically conductive, a non magnetically permeable material, e.g., stainless steel, or (as discussed above) a barrier material that can be partially saturated in a controlled manner to serve as a magnetic antenna or magnetic lens directing oscillating magnetic flux into the rail 100.

Figure 4B:
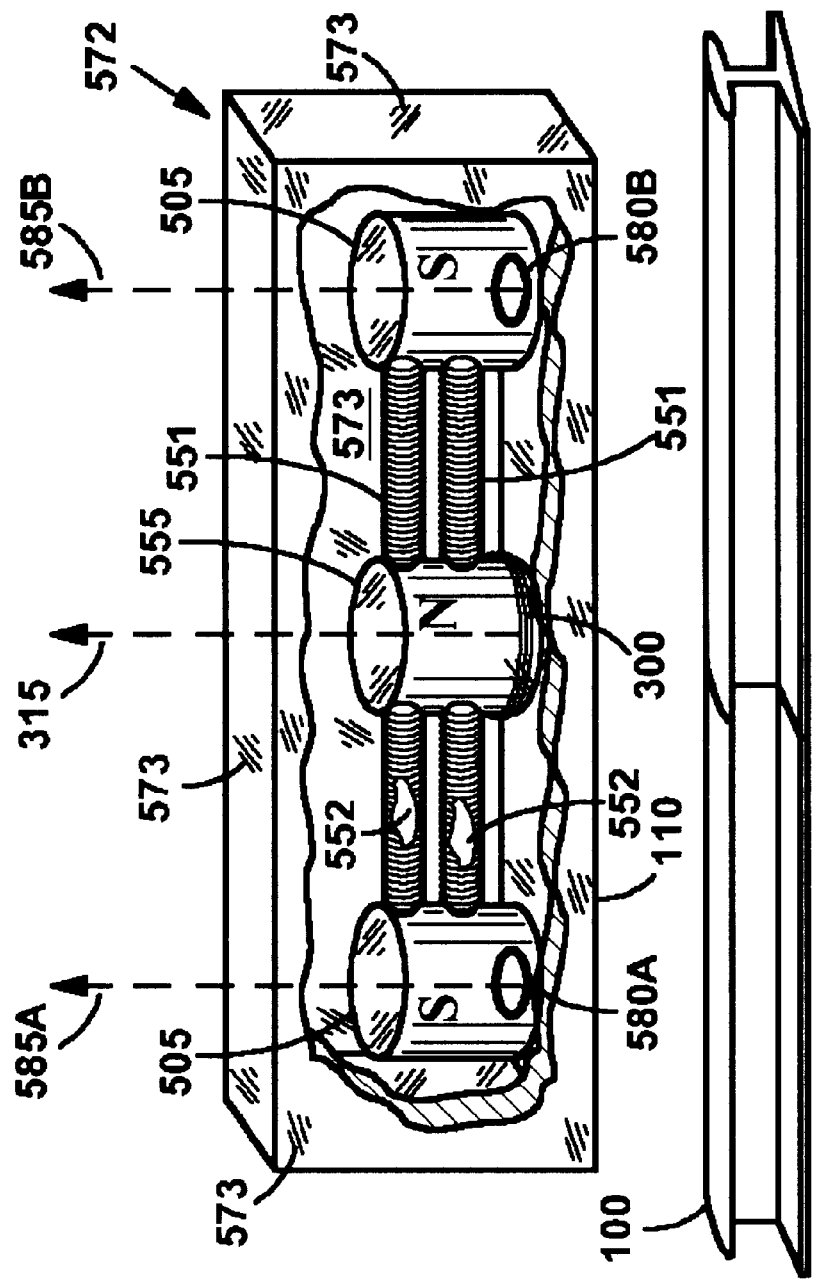

FIG. 4B illustrates a configuration wherein the transmitter 300 is wrapped around the circumference of a culminator 555, serving as the combined pole (here designated as the north pole) opposed by two separate poles 505A and 505B.

In this configuration each pole 505A and 505B opposing the culminator 555 contains a receiver coil 580A and 580B. The center axis of the receiver coils and transmitter coil are parallel. It will accordingly be appreciated that in this configuration, transmitter and receivers are not geometrically nulled. The axis of the receivers and the transmitter are orthogonal to the axis of each saturation coil 551 wrapped upon saturation core 552. It will also be appreciated that, as a result of the single component culminator 555 containing two like poles and the resulting bucking of flux lines, the greatest concentration of magnetic flux will be proximate to the culminator 555. Magnetic flux proximate to each pole 505A and 505B may also serve to partially saturate a proximate area of the rail 100 to facilitate the reception of oscillating flux induced by the eddy currents in the target rail.

Figure 5:
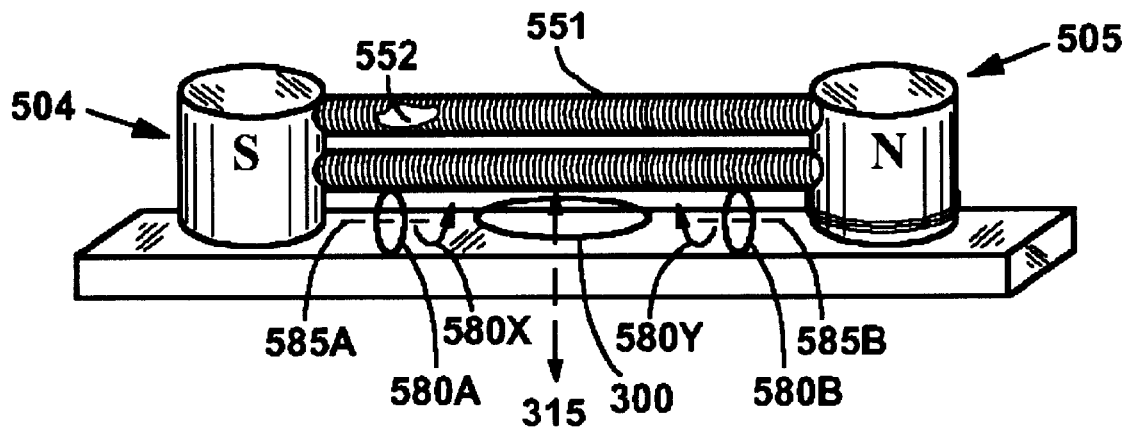
FIG. 5 illustrates another embodiment of the subject invention.

FIG. 5 illustrates a configuration wherein the receiver coils 580A and 580B and the transmitter coil 300 are placed separate from the poles 504 and 505. It will be appreciated that this configuration is advantageous as a result of the geometry of the field lines (not shown) of the saturation flux existing between the poles 504 and 505. The receivers 580A and 580B are each geometrically nulled to the transmitter. Note that the center axis of the receivers 585A and 585B are orthogonal to the center axis 315 of the transmitter 300. They may be each electronically nulled by having opposing direction of winding as shown by vector lines 580X and 580Y.

Figure 6:
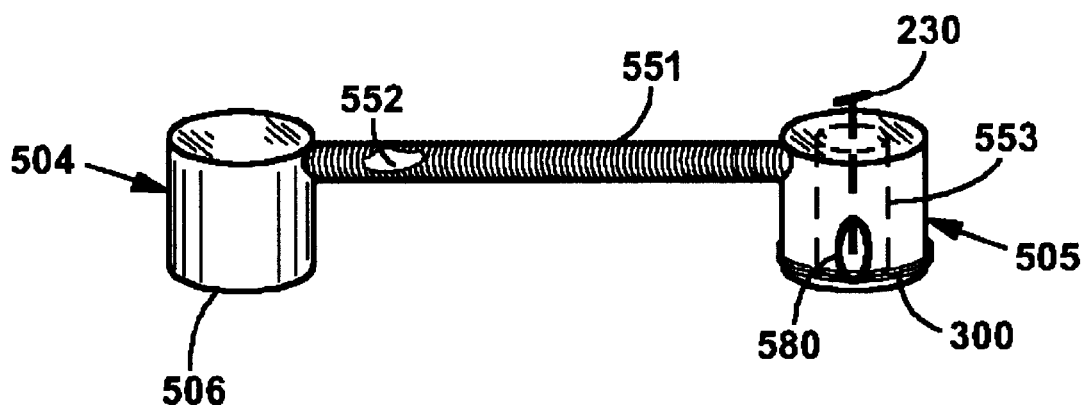
FIG. 6 illustrates another embodiment of the subject invention.

FIG. 6 illustrates yet another configuration wherein the transmitter 300 and the receiver 580 are located within the same magnetic pole. The receiver, located within the pole 505, is geometrically nulled to the transmitter. The position of the receiver coil may also be maneuvered within the cavity 553 by means of sub-components 230. This combined nulling and maneuverability facilitates the reception of signals from the track (not shown). It will be appreciated that the transmitter is also geometrically nulled to the saturation coil 551.

Figure 7:
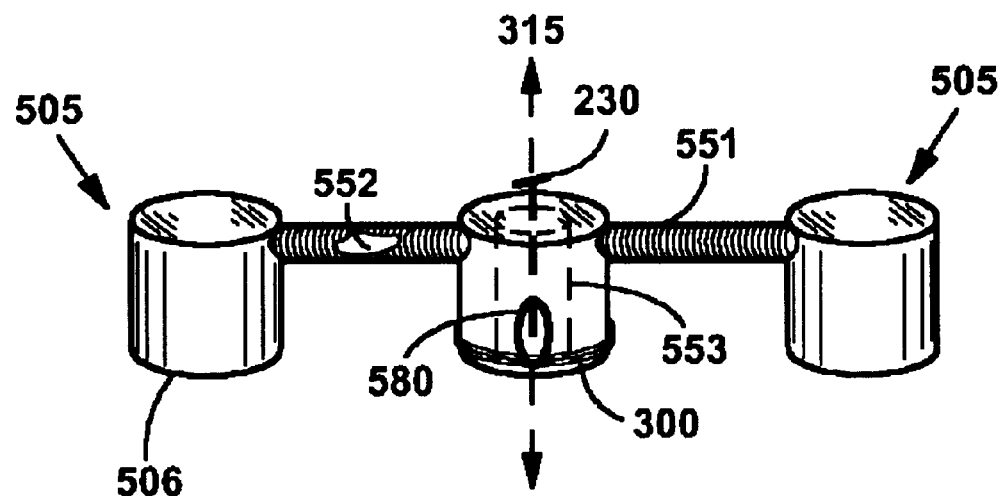
FIG. 7 illustrates another embodiment of the subject invention.

FIG. 7 illustrates the nulled positioning of the receiver 580 within a culminator 555 containing the transmitter coil 300. It will be appreciated that the location of the transmitter and receiver are proximate to the location where the greatest concentration of flux lines engaging the track (not shown) will be located. This configuration can be expected to provide enhanced energy efficiency. Again, the transmitter coil 300 is located upon the outer surface of the culminator 555. This allows the transmitter coil 300 to have the same magnetic moment geometry as the culminator 555, further enhancing efficiency. The adjustable position of the receiver within the cavity 553 of the culminator by receiver adjustment means 230 permits the receiver to be nulled to both the transmitter 300 and the saturation coils 551.

Figure 8:
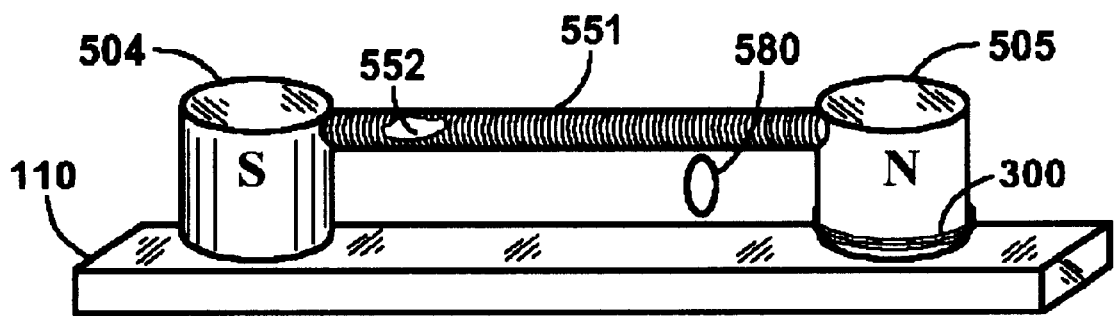
FIG. 8 illustrates another embodiment of the subject invention.

FIG. 8 further illustrates another embodiment of the receiver and transmitter used in the sensor tool subject of the invention.

Figure 9A:
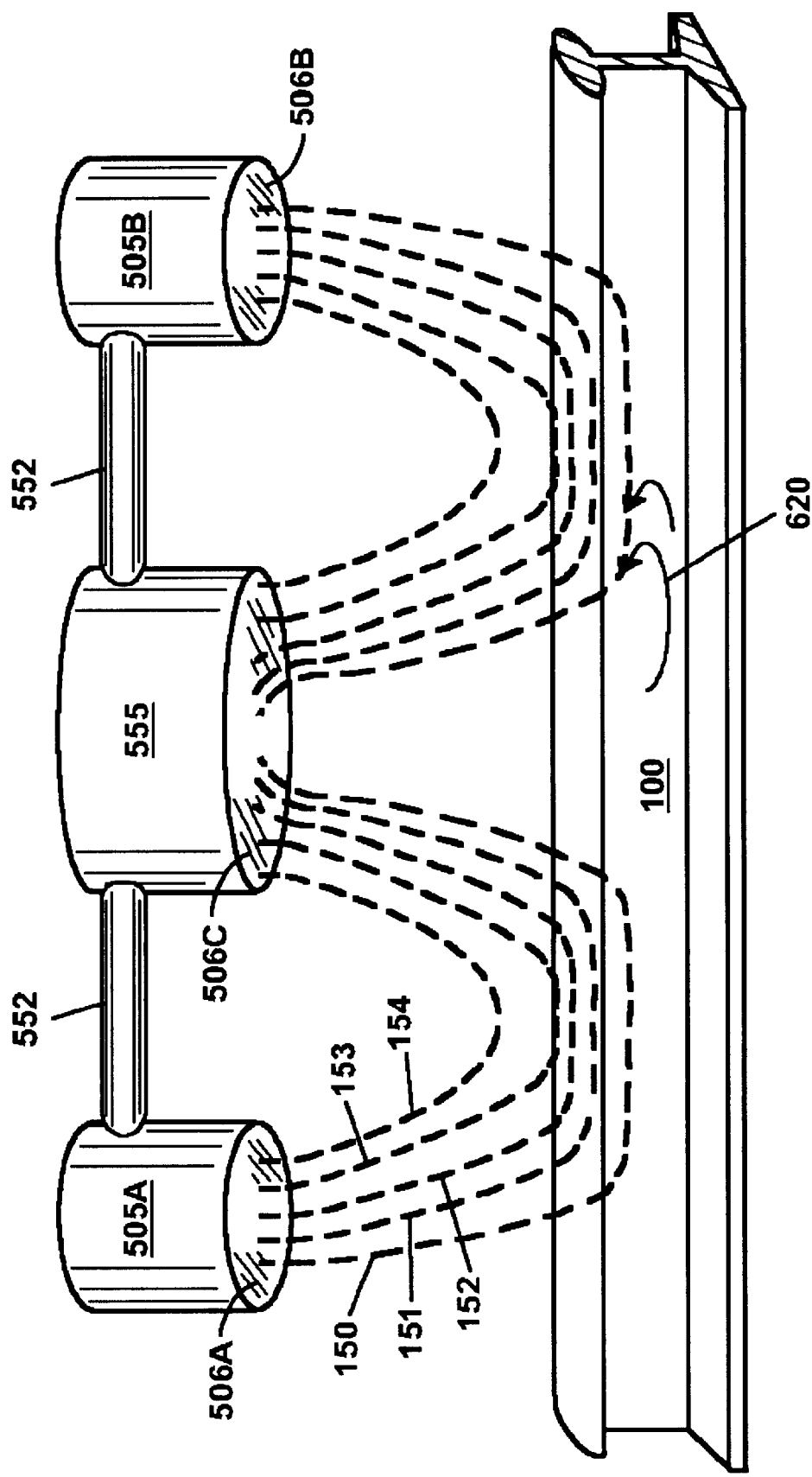
FIG. 9A illustrates the combined saturation and transmitter flux field interacting with the target rail.

FIG. 9A illustrates a magnetic saturation generator comprised of culminator 555, the two magnetic poles 505A and 505B having a polarity opposing that of the culminator, and the saturation cores 552A and 552B. The transmitter, saturation coil and receiver are not illustrated. Also illustrated in the magnetic flux field 150–154 comprised of the magnetic flux generated by the saturation coil wrapped around the saturation core 552A and 552B, and the oscillating, higher frequency transmitter flux generated by transmitter coil that may be wrapped around the exterior of the culminator 555. It will be appreciated that the flux field continues within the structure of the poles, saturation core and culminator to form a closed loop of a magnetic flux field. It will also be appreciated that the flux exits at the surfaces of the generator primarily as illustrated 506A, 506B and 506C. The area of greatest flux density will be in an area proximate to (but apart from) the center of the culminator. In this location, the permeability of the culminator will be most greatly reduced, causing the field lines to be emitted from the surface 506C at an angle less than 90°. This angled flux is shown most dramatically in the field line 150 proximate to the surface 506C of the culminator 555. Since field lines repeal each other and may not cross, the field lines emanating from the region of the culminator have the lowest permeability will push the other field lines, creating more compact and greater directionality. This is illustrated by the two groups of field lines coupling with the rail 100.

FIG. 9B also illustrates the magnetic flux lines 150–154 created of the combined saturation flux and oscillating transmitter flux. It will be appreciated that the flux field shifts as the polarity of the ac powered component of the flux field shifts. This can also be achieved by pulsing the transmitter power since the density of the combined flux will change with the "on/ofF" pulsing. Also shown is the eddy current 620 generated within the target rail 100. The oscillating flux, created by the oscillating or pulsed powered transmitter, induces this eddy current 620. Of course, the eddy current also induces a separate oscillating flux 140–143 that may be detected by the receiver (not shown). Among the advantages of this configuration are the geometric nulling of the transmitter, receiver and saturation coils, the spatial nulling between the receiver and transmitter and the concurrent optimized position of the transmitter and receiver to locations of greatest partial saturation of the target rail. It will be appreciated that the receiver may be adjustably located within the culminator.

Figure 9C:
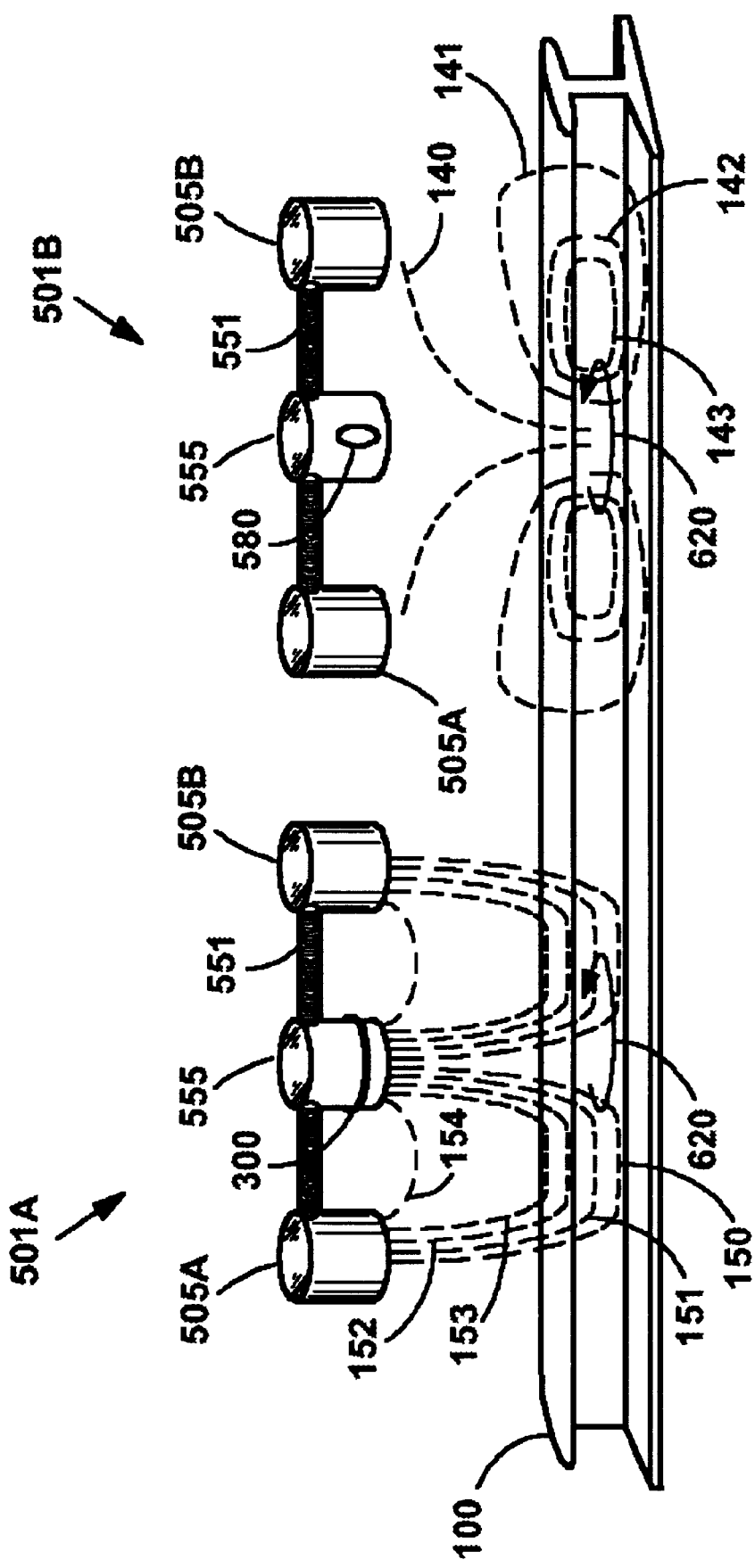
FIG. 9C illustrates an embodiment of the subject invention utilizing two sensors.

FIG. 9C illustrates a configuration wherein the transmitter 300 and receiver 580 are located on separate magnetic flux culminators 555A and 555B. Each culminator is part of a separate magnetic saturation generator 501A and 501B comprised of two like poles 505A and 505B and saturation coils 551. Each saturation flux generator can be separately powered and controlled. Although the magnetic flux field 150–154 is illustrated for one magnetic saturation generator 501A only, it will be appreciated that both the transmitter and receiver are each placed in a location proximate to the greatest concentration of saturation flux of the generator 501A and 501B respectively engaging with the target rail 100. FIG. 9C also illustrates the oscillating magnetic field 140–143 induced within the rail by the eddy current 620. The eddy current 620 is generated within the rail by the penetration of oscillating magnetic flux generated by the transmitter 300 and comprising part of the flux field 150–154. It will be appreciated that much of this oscillating magnetic flux 140–143 remains within the partially saturated rail 100. The component of the flux field comprised of the oscillating transmitter flux will generate eddy currents 620 within the electrically conductive rail. It will also be appreciated that as the higher frequency oscillating transmitter flux reverses polarity, the intensity and shape of the flux field will change. Reference is made to FIG. 2C.

Figure 10:
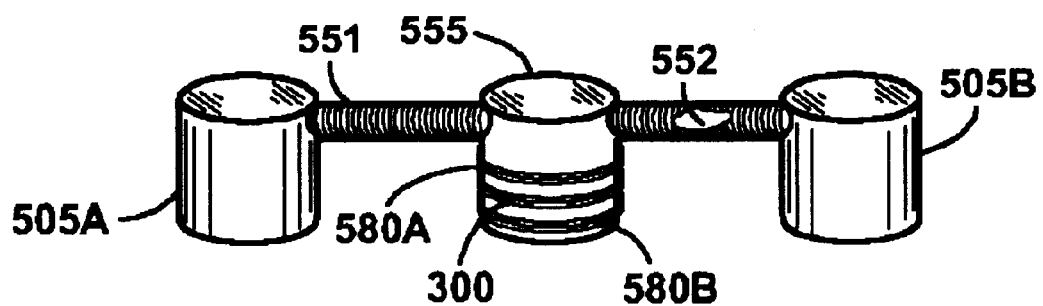
FIG. 10 illustrates another embodiment of the subject invention utilizing multiple receivers and a single transmitter.

FIG. 10 illustrates a configuration wherein two receiver coils 580A and 580B are spaced equidistant from the transmitter coil 300. The coils are located on the outer circumference of the culminator 555. The opposing poles 505A and 505B are connected to the culminator by the saturation cores 552 around which the saturation coils 551 are wound. The receiver coils and the transmitter coil each have the same axis of rotation. However, the receiver coils can each be wound in opposing directions, thereby nulling each signal received from the transmitter. In view of the differing location of each receiver coil to the target rail and the magnetic flux emitted by the eddy currents generated within the rail, each coil will detect a distinct signal from the rail.

Figure 11:
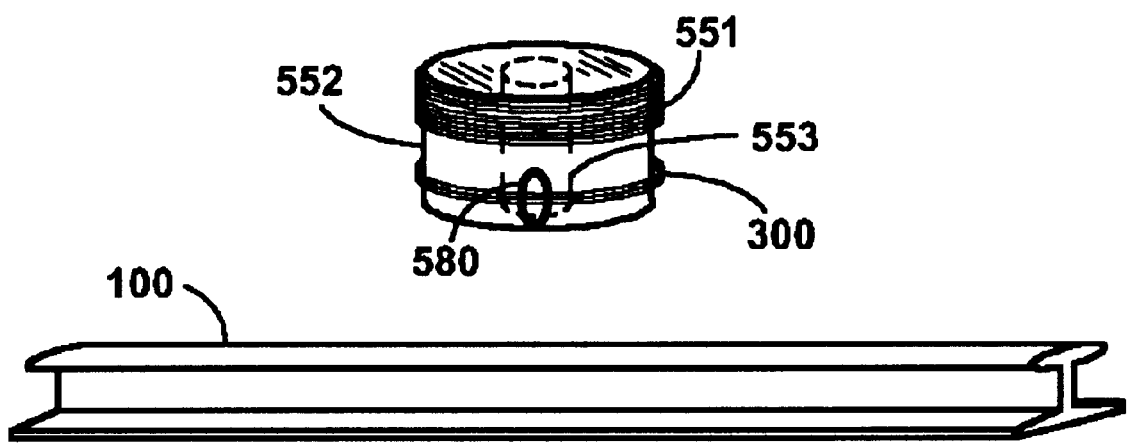
FIG. 11 illustrates another embodiment of the subject invention.

FIG. 11 Illustrates yet another embodiment wherein the magnetic saturation generator comprises a single core 552 upon which the saturation coil 551 is wound. The transmitter coil 300 is also wound on the outer circumference of the core but proximate to the target rail 100. The transmitter coil accordingly has the same magnetic moment region as the saturation coil 551. The receiver coil 580 is adjustably located within the center cavity 553 of the core 552. The receiver coil 580 can be nulled to the transmitter coil and saturation coil.

Figure 12:
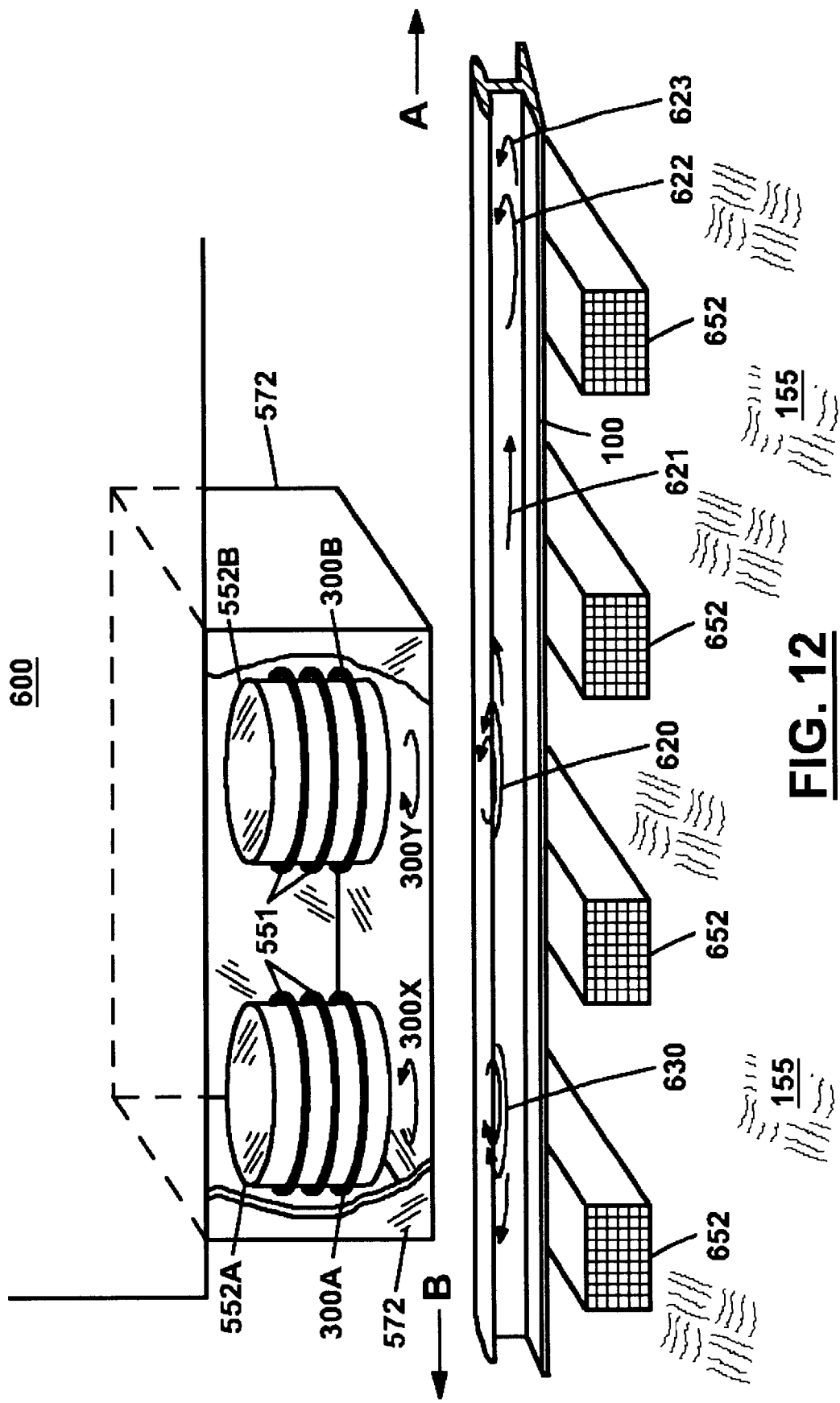
FIG. 12 illustrates the use of two bucking transmitters to enhance the transmission of signal through the rails ahead of the train.

FIG. 12 illustrates an embodiment wherein two saturation cores 552A and 552B are consecutively placed above the target rail 100 parallel to the longitudinal axis A B of the rail 100. The saturation cores 552A, 552B are located in a housing 572 mounted on a rail car or locomotive 600. Around each saturation core is wound a saturation coil 551. Also wound around each core is a transmitter coil 300A and 300B. Each transmitter coil is wound in opposing direction as indicated by vector lines 300X and 300Y.

Figure 13:
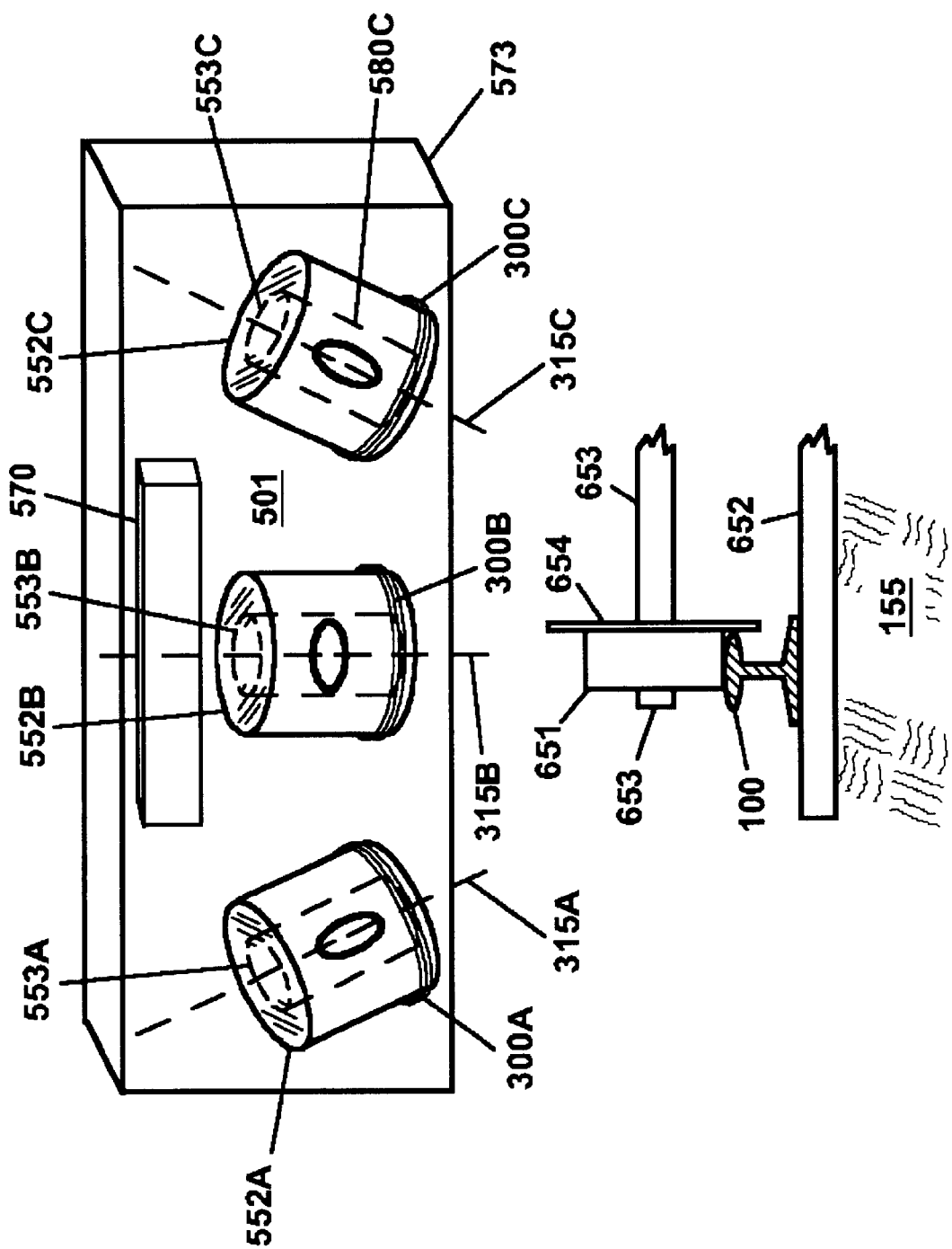
FIG. 13 illustrates alternate positioning of components to provide more efficient or simultaneous multi-perspective rail inspection.

Each transmitter coil, generating a pulsed or oscillating current, will generate eddy currents within the rail. The eddy currents 620 and 630 will be in opposing directions. In a preferred embodiment, the eddy currents 620, 630 will oscillate at the same frequency but, due to the opposing orientation, will buck (repeal) each other. This will cause the eddy currents to assume a more elliptical form and extending further along the length of the rail. This causes the eddy currents to be pushed further out along the axis AB as shown by the eddy currents 620–623. Of course, as the field of the oscillating eddy currents extends further along the track (and in one direction ahead of the moving train; thereby adding further movement as the pulsed or oscillating field couples with the stationary but electrically conductive rail), a corresponding oscillating magnetic flux is also induced further ahead of the train. FIG. 13 illustrates another embodiment of the sensor tool subject of the invention. Three separate saturation cores 552A, 552B and 552C are placed in a series having an axis orthogonal to the longitudinal axis of the target rail 100. The saturation cores 552A, 552B, 552C each are directed to the rail. This configuration permits multiple signals to be simultaneously directed to the same portion of the rail. The orientation of each signal will be different, i.e. the signal received by the receiver 580A within saturation core 552A will be oriented to the outer side of the rail. The orientation of the signal detected by receiver 580B will be from directly above the rail surface. The receiver 580C will detected a signal oriented from the inner side of the rail. The varied orientation will facilitate a more complete view or scan of the rail since some defects may be more difficult to detect due to orientation to a single sensor. It will be appreciated that the train wheel 651, comprising the inner flange 652, outer wheel hub 653 and axle 654, is depicted to illustrate the location of the inner and outer sides of the rail 100. It is not necessary that the sensor tool 500 be located above the train wheel.

Figure 14:
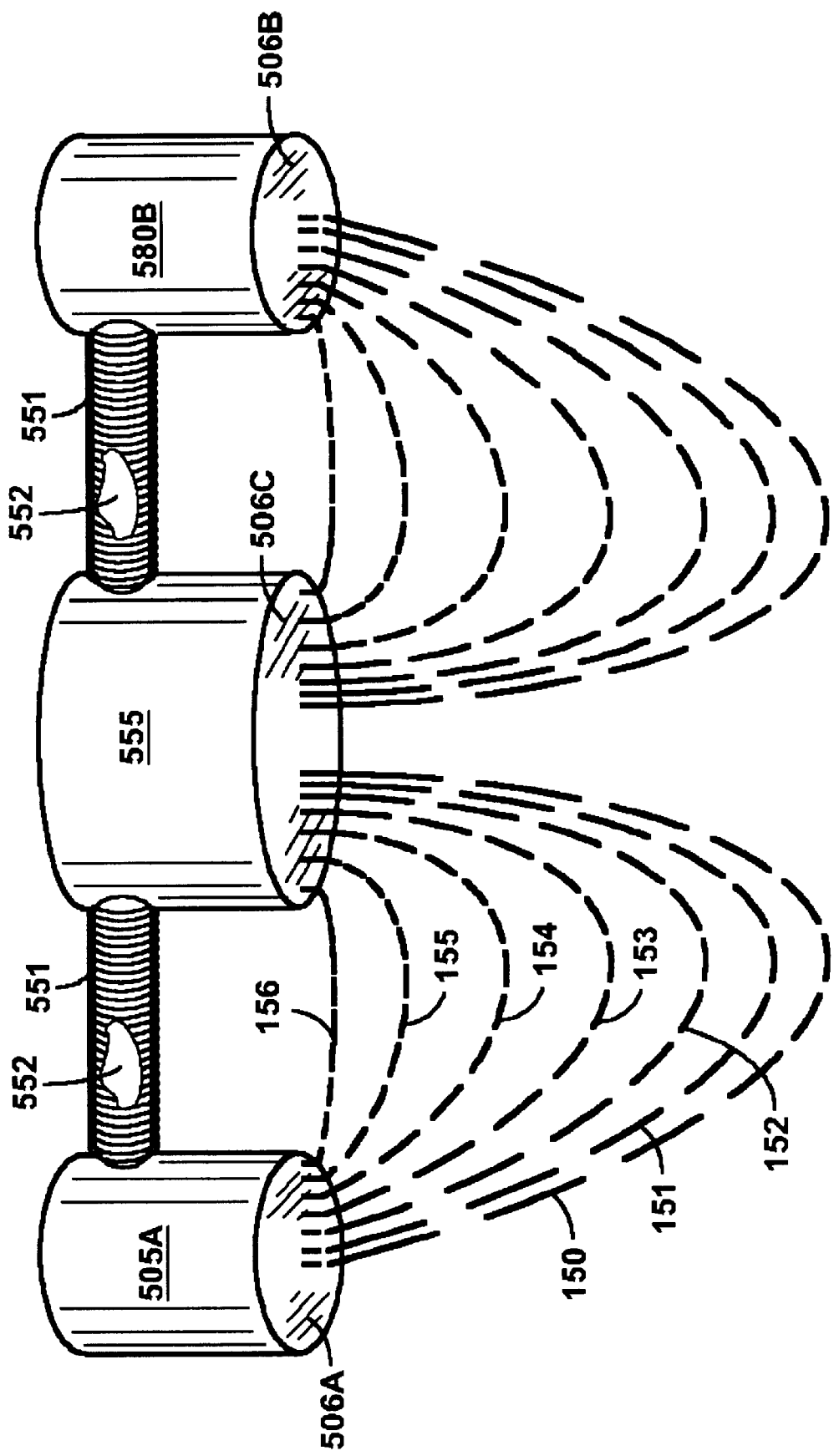
FIG. 14 illustrates the magnetic flux field produced by an embodiment of a magnetic saturation generator.

FIG. 14 provides another illustration of the saturation flux emanating from the surface 506A, 506B and 506C to the saturation flux generator. It will be appreciated that the greatest density of magnetic flux will be proximate to, but apart from, the center of the culminator 555. This is a function of the mutual repulsion of the like magnetic fields within the culminator 555. This results in the asymmetric pattern or geometry of each field between the culminator 555 and the proximate opposing pole 505A and 505B respectively. Of course, the flux field continues within each pole, saturation core 551 and returning to the culminator 555.

Figure 15A:
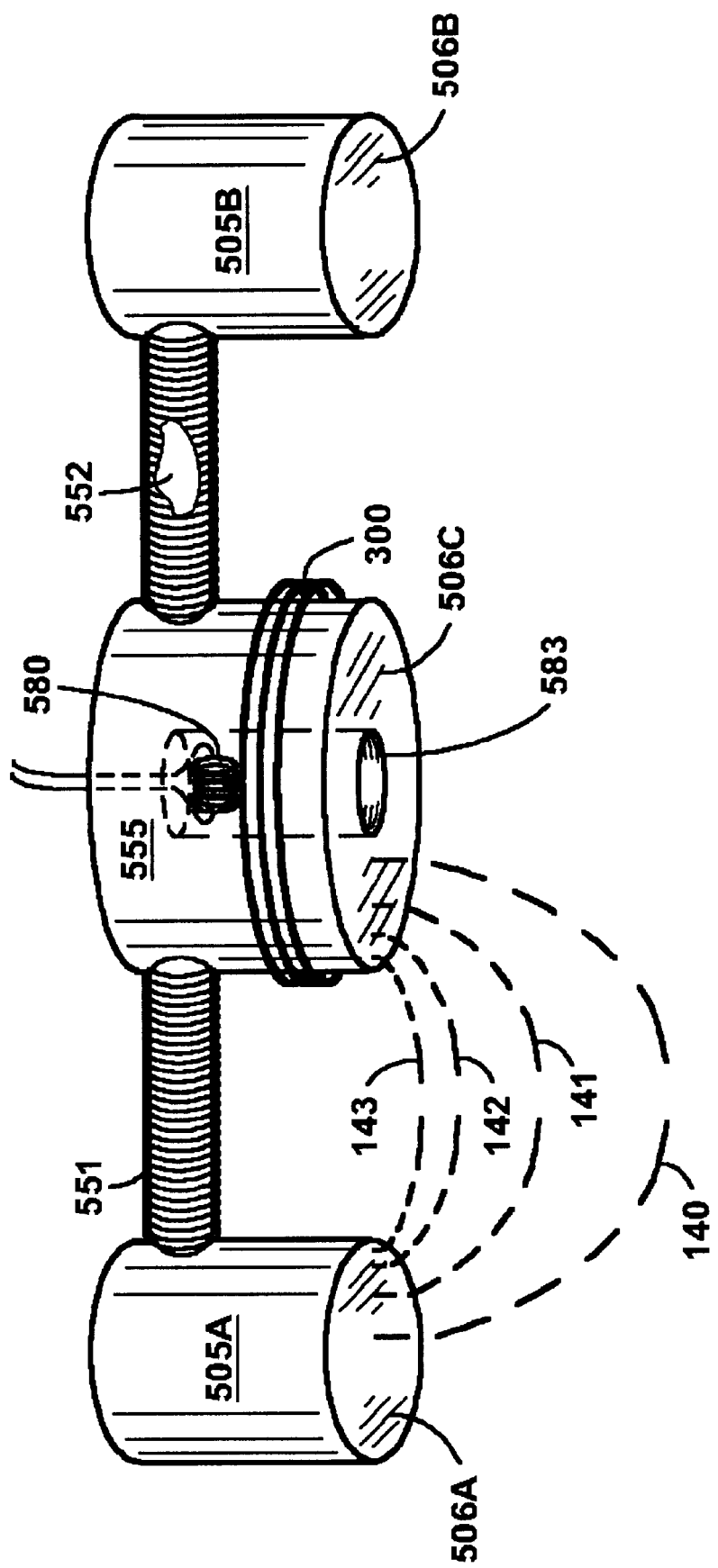
FIG. 15A illustrates the magnetic flux field produced by the transmitter of one embodiment of the invention.

FIG. 15A illustrates the oscillating flux field emanating primarily from surface 506C of the culminator 555 and extending to the opposing pole 505A. It will be appreciated that a similar field exists between the culminator 555 and pole 505B. Since the flux field shown in FIG. 15A is illustrated independent of saturation flux, the greatest flux density will be proximate to the outer edge of the culminator 555 and the flux emanating from the surfaces 506A and 506C respectively will follow a relatively shallow path to the opposing pole within the pole 505A.

Figure 15B:
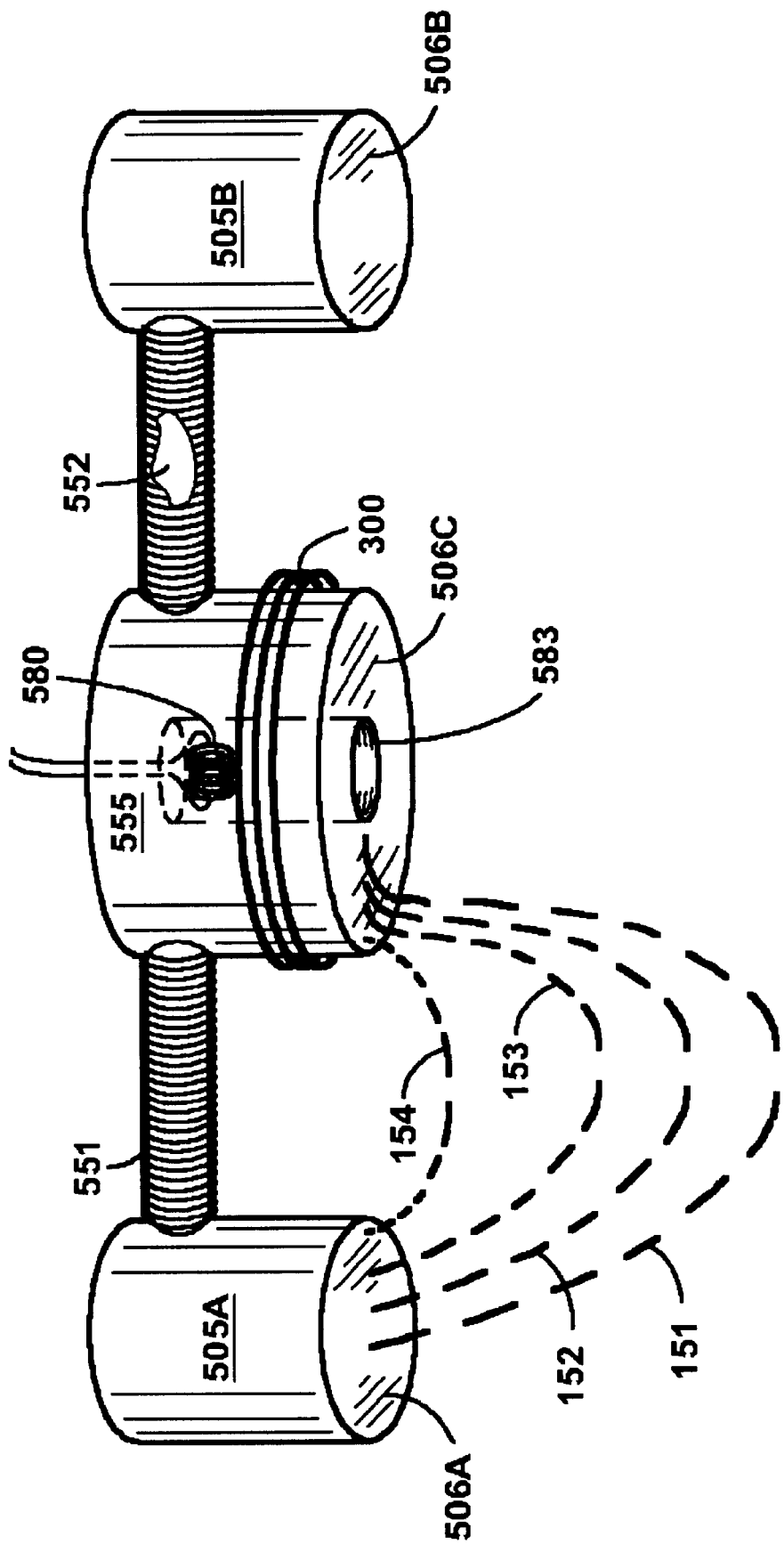
FIG. 15B illustrates a portion of the flux field comprised of combined saturation and transmitter magnetic flux.

FIG. 15B is an additional illustration of the combined saturation and transmitter flux 151–154. This flux filed exhibits the asymmetric geometry with the greatest concentration of flux proximate to the culminator 555. The flux field extends in a relatively single direction approximately orthogonal to the culminator surface 506C. It will be appreciated that this geometry differs from the typical rapid dispersion of magnetic flux.

The elements that these several embodiments all have in common are the following.

1. Magnetic Saturation Generators

The magnetic saturation generators, utilized to partially saturate the target rail (particularly the rail surface and thereby reducing the permeability of the rail) may be permanent magnets, dc powered electromagnets or AC powered electromagnets and generating a relative low frequency relation to the transmitter frequency. This difference in frequency is intended to allow multiple wavelengths of transmitter flux (ac powered) to measure the rail during each partial saturation phase.

The magnetic flux field must be of sufficient density at the surface of the target rail to partially reduce the permeability of the target rail. The reduction of the target rail permeability (particularly at the rail surface) must be of a sufficient magnitude to allow a significant portion of the oscillating electromagnetic transmitter flux to be absorbed into the target rail surface. The range of partial saturation is within a measured relative permeability of approximately 50 to a value greater than 1. (Although permeability is measured in units of webers/amp, relative permeability does not have units.) Note that at $\mu=1$, the electromagnetic barrier material is deemed to have achieved totally saturated This magnetic flux must be of sufficient density at a north and south pole separation of 1 L to 2 L, where L is the distance from the magnetic poles to the surface of the target track.

2. Transmitter

The transmitter may be wound on a separate core of ferromagnetic material. However, it has been found that because of the Magnetic™ effect, it is more effective for the transmitter to be wrapped on the saturating core and with both the saturation coil and the transmitter coil having the same diameter.

It is preferred to have the transmitter in the middle of the magnetic flux field creating the partial saturation of the target rail. In this way, the maximum quantity of transmitter flux engages with the target rail in an area of reduced permeability.

It is also possible to separately place the transmitter and receiver in a configuration with different magnetic saturation generators and each creating different areas of partial saturation in the rail target. Without magnetic lens focus, the space between magnets creating the separate areas of partial saturation may be (optimally) approximately twice the distance from the surface of each magnet to the surface of the target rail.

3. The Receiver

The receiver coil may be wound on a core. In a preferred embodiment, the receiver coil is wrapped around the saturation core, thereby utilizing the increased apparent magnetic moment of the saturation core.

The receiver is nulled geometrically with respect to the transmitter. There are many ways to perform a geometric null. A few of these are as listed below:

a) The axis of the receiver coil rotated 90° from the axis of the transmitter coil.

b) Two transmitter coils with one receiver coil with the winding of the transmitter coils bucked and the axis of the receiver orthogonal to the axis of the transmitter coils.

c) One transmitter, two bucked receivers with or without the axis rotated 90° to the axis of the transmitter. Axis d) One transmitter with two coaxial receiver coils wound in opposing or bucked direction with respect to each other e) One transmitter coil with a receiver coil inside the diameter of the transmitter coil but having its axis rotated 90° with respect to the axis of the transmitter coil.

f) Multiple combinations of transmitters and receivers nulled with respect to each other.

4. Shielding for EM External Sources (Physical and Electronic)

There are many situations in which the subject invention may be anticipated to experience large external magnetic fields. This can be expected to occur in the vicinity of large current switching to electric motor field coils. In such applications, shielding using materials that are highly magnetically permeable (i.e. greater than 2000 webers/amps) should be used. In the simplest case, a box of carbon steel plate around five sides of the sensor can be used. The sides of these plates may extend below the transmitters and receivers or other coils or structures that may act as antennas).

In a preferred embodiment, the transmitter frequency (or frequencies) will be chosen from a range different from the frequencies anticipated to be experienced from external sources. In another preferred embodiment, the electronic components themselves, along with the wiring should be protected against current surges.

The bottom protective cover to the subject invention that is nearest to the track may be made of stainless steel, aluminum or some other material that is not magnetically permeable. In this way the power needed to saturate the metal for a transparency can be conserved.

Method of Operation

The method of operation is straight forward and may be described as follows:

The dc or low frequency oscillating magnetic field coils are activated. The large magnetic field has a sufficient flux density at the surface of the target rail to lower the permeability of the ferromagnetic rail, e.g., from approximately 2000 webers/amp to a relative permeability of 5, 10 or 20. This is made to occur in order that the coefficient of reflection ($C_R$) is reduced.

$$C_R = (\mu_{(ferromagnetic\ steel)} - \mu_{(air)}) / (\mu_{(ferromagnetic\ steel)} + \mu_{(air)})$$

If $C_R$=1—then total reflection occurs. If $C_R$=0, then no reflection occurs. Since $\mu_{(air)}$=1 and $\mu_{(ferromagnetic\ steel)}$=2000 to 6000, it is evident why an electromagnetic wave would not significantly couple or engage with a railroad track since $C_R$=1. However, if the target's relative permeability is reduced to 5 say, then coefficient of reflection is significantly less than 1, i.e., $$C_R = 4/6 = 2/3$$

Accordingly, approximately one third of the emitted transmitter flux signal is absorbed into the railroad track. This has been found to be of sufficient energy to generate the eddy currents needed for detection of cracks or other anomalies in the target track. In a preferred embodiment, a saturating magnet powered by dc current is used in conjunction with a transmitter continuously emitting at least one oscillating signal.

The oscillating frequencies utilized have been up to 5 kilohertz. At a train speed of 100 ft/second, approximately 50 wavelengths of oscillating electromagnetic signal will be transmitted for each foot of target rail. In preferred embodiments of the invention, high-speed electrical data processing instruments are utilized to enhance the invention for use with high train speeds.

2. Moreover permeability curves have a very rapid rise in saturation with respect to changes in the H field. This means that very small changes in the "H" (amp turns) yields large changes in the magnetic field "β" expressed in webers/meter squared. Also the curve shows that complete saturation of 1 is an asynstotic phenomenon and hard to achieve.

3. Once a spectrum of eddy currents are induced into the target rail they will yield a constant phase and amplitude (as seen by the receiver) over smooth track or metallic surface. However, when a discontinuity such as a crack is encountered, then there is a build up of eddy currents at the crack which are seen as an amplitude increase. After the transmitter has passed over to the crack, then the phase will change on the received frequency. This is due to the capacitor effect. Both the amplitude and phase angle change are proportional to the size of the crack or discontinuity. These amplitude and phase signatures vary for a number of different anomalies and thus they can be catalogued and compared to each other. Combined with a GPS system, this data could provide information of both the location and nature of detected anomalies in the track, thereby making track repair more efficient and enhancing the safety and efficiency of railroads.

4. Multi-frequencies have been found to be useful. For example, lower frequency electromagnetic signals penetrate deeper into the target rail. This is consistent with the common experience of low frequency sound incurs less attenuation through barriers than higher frequency sound. Accordingly, the use of a multiple range of frequencies, e.g., 30 Hz, 500 Hz, and 2000 Hz, would provide a good profile of the object at various depths for anomaly detection and inspection.

In another embodiment, it has been demonstrated that the transmitter and receiver may be widely separated, each proximate to separate magnetic saturation generators and creating partially saturated regions within the rail This can enhance power conservation.

Further modifications and alternative embodiments of this invention will be apparent to those skilled in the art in view of this specification. Accordingly, this specification is to be construed as illustrative only and is for the purpose of teaching those skilled in the art the manner of carrying out the invention. It is to be understood that the forms of the invention herein shown and describe are to be taken as the presently preferred embodiments. Various changes may be made in the shape, size and arrangement of parts. For example, equivalent elements may be substituted for those illustrated and described herein and certain features of the invention may be utilized independently of the use of other features, all as would be apparent to one skilled in the art after having the benefit of this description of the invention.

I claim:

1. A method for determining the characteristics of a railroad track comprising the steps of:
    (a) creating a first electromagnetic wave adjacent to the track,
    (b) saturating, at least partially, the track with the first electromagnetic wave,
    (c) creating a second electromagnetic wave having a frequency higher than the first electromagnetic wave, and
    (d) engaging the second electromagnetic wave with the track when the track is at least partially saturated for creating a resulting wave which resulting wave is available for detection such that upon detection a received signal is created that has a nulled relationship to the second electromagnetic wave whereby the characteristics of the track are discernable from the received signal.

2. A method for determining the characteristics of a railroad track, the method comprising the steps of:
    (a) lowering the permeability of the track with an initial electromagnetic wave,
    (b) creating a transmitted electromagnetic wave adjacent to the track having a frequency higher than the initial electromagnetic wave,
    (c) engaging the transmitted electromagnetic wave with the track for creating a resulting wave, and
    (d) detecting the resulting wave for creating a received signal that has a nulled relationship to the transmitted wave, and
    (e) evaluating the received signal to determine the characteristics of the track.

3. The method for determining the characteristics of a railroad track defined in claim 2 wherein the step of creating the resulting wave available for detection so as to create a received signal that has a nulled relationship to the transmitted wave comprises geometrically nulling.

4. The method for determining the characteristics of a railroad track defined in claim 2 wherein the step of geometrically nulling comprises creating the transmitted wave so as to prevent coupling with the received signal.

5. The method for determining the characteristics of a railroad track defined in claim 2 wherein the step of creating the resulting wave available for detection so as to create a received signal that has a nulled relationship to the transmitted wave comprises separation nulling.

6. The method for determining the characteristics of a railroad track defined in claim 2 wherein the step of creating the resulting wave available for detection so as to create a received signal that has a nulled relationship to the transmitted wave comprises electronic nulling.

7. The method for determining the characteristics of a railroad track defined in claim 2 wherein the step of electronic nulling comprises nulling the transmitted electromagnetic wave and the received signal by degrees of phase.

8. The method for determining the characteristics of a railroad track defined in claim 2 wherein the step of electronic nulling comprises nulling the transmitted electromagnetic wave and the received signal by amplitude.

9. The method for determining the characteristics of a railroad track defined in claim 2 wherein the step of electronic nulling comprises nulling the transmitted electromagnetic wave and the received signal by degrees of phase and amplitude.

10. The method for determining the characteristics of a railroad track defined in claim 2 wherein the step of nulling comprises minimizing direct signal coupling between the transmitted electromagnetic wave and the received signal.

11. The method for determining the characteristics of a railroad track defined in claim 2 wherein the step of lowering the permeability of the track with an initial electromagnetic wave comprises using a range of frequencies above zero.

12. The method for determining the characteristics of a railroad track defined in claim 2 wherein the step of lowering the permeability of the track with an initial electromagnetic wave comprises using a DC wave for the initial electromagnetic wave.

13. The method for determining the characteristics of a railroad track defined in claim 2 wherein the step of lowering the permeability of the track with an initial electromagnetic wave comprises using an AC wave for the initial electromagnetic wave.

14. The method for determining the characteristics of a railroad track defined in claim 2 wherein the step of evaluating the received signal to determine the characteristics of the track comprises determining the resistivity of the track.

15. The method for determining the characteristics of a railroad track defined in claim 2 wherein the step of evaluating the received signal to determine the characteristics of the track comprises detecting interfaces in the track.

16. A method for determining the characteristics of a railroad track comprising the steps of:
    (a) lowering the permeability of the track with an initial electromagnetic wave,
    (b) creating a transmitted electromagnetic wave adjacent to the track having a frequency higher than the initial electromagnetic wave,
    (c) engaging the transmitted electromagnetic wave with the track for creating a resulting wave, and
    (d) making the resulting wave available for detection so as to create a received signal that has a nulled relationship to the transmitted wave for evaluating the characteristics of the track.

17. The method for determining the characteristics of a railroad track defined in claim 16 wherein the step of making the resulting wave available for detection so as to create a received signal that has a nulled relationship to the transmitted wave comprises geometrically nulling.

18. The method for determining the characteristics of a railroad track defined in claim 16 wherein the step of geometrically nulling comprises creating the transmitted wave so as to prevent coupling with the received signal.

19. The method for determining the characteristics of a railroad track defined in claim 16 wherein the step of making the resulting wave available for detection so as to create a received signal that has a nulled relationship to the transmitted wave comprises separation nulling.

20. The method for determining the characteristics of a railroad track defined in claim 16 wherein the step of making the resulting wave available for detection so as to create a received signal that has a nulled relationship to the transmitted wave comprises electronic nulling.

21. The method for determining the characteristics of a railroad track defined in claim 20 wherein the step of electronic nulling comprises nulling the transmitted electromagnetic wave and the received signal by degrees of phase.

22. The method for determining the characteristics of a railroad track defined in claim 20 wherein the step of electronic nulling comprises nulling the transmitted electromagnetic wave and the received signal by amplitude.

23. The method for determining the characteristics of a railroad track defined in claim 16 wherein the step of nulling comprises minimizing direct signal coupling between the transmitted electromagnetic wave and the received signal.

24. The method for determining the characteristics of a railroad track defined in claim 16 wherein the step of lowering the permeability of the track with an initial electromagnetic wave comprises using a range of frequencies of zero and above.

25. The method for determining the characteristics of a railroad track defined in claim 16 wherein the step of lowering the permeability of the track with an initial electromagnetic wave comprises using a DC wave for the initial electromagnetic wave.

26. The method for determining the characteristics of a railroad track defined in claim 16 wherein the step of lowering the permeability of the track with an initial electromagnetic wave comprises using an AC wave for the initial electromagnetic wave.

27. An apparatus for determining the characteristics of a railroad track, the apparatus comprising:
   (a) means for lowering the permeability of the track with an initial electromagnetic wave,
   (b) a transmitter for generating a transmitted electromagnetic wave and engaging the transmitted electromagnetic wave with the track for creating a resulting wave,
   (c) a receiver for detecting the resulting wave such that the receiver is nulled with respect to the transmitter, the receiver for creating a received signal, and
   (d) means for evaluating the received signal to determine the characteristics of the track.

* * * * *